(12) United States Patent
Roth et al.

(10) Patent No.: US 8,268,564 B2
(45) Date of Patent: Sep. 18, 2012

(54) METHODS AND APPLICATIONS FOR STITCHED DNA BARCODES

(75) Inventors: Frederick P. Roth, Newton, MA (US); Yo Suzuki, Roxbury Crossing, MA (US); Joseph Mellor, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 408 days.

(21) Appl. No.: 12/236,912

(22) Filed: Sep. 24, 2008

(65) Prior Publication Data

US 2009/0098555 A1 Apr. 16, 2009

Related U.S. Application Data

(60) Provisional application No. 61/049,134, filed on Apr. 30, 2008, provisional application No. 60/975,354, filed on Sep. 26, 2007.

(51) Int. Cl.
*C12P 19/34* (2006.01)
(52) U.S. Cl. ........................................................ 435/6.12
(58) Field of Classification Search .................. None
See application file for complete search history.

(56) References Cited

U.S. PATENT DOCUMENTS

| | | | | |
|---|---|---|---|---|
| 7,749,697 | B2 * | 7/2010 | Oleksiewicz et al. | 435/6 |
| 2007/0161031 | A1 * | 7/2007 | Trinklein et al. | 435/6 |
| 2008/0014589 | A1 * | 1/2008 | Link et al. | 435/6 |

OTHER PUBLICATIONS

Wetmur et al. (2005) Nucleic acid Research vol. 33 No. 8: 2615-2619.*
Turner et. al. (published on line May 23, 2006) Nature Methods vol. 3 No. 6 pp. 439-445.*
Giaver G et al. Functional profiling of the *Saccharomyces cerevisiae* genome. Nature, Jul. 25, 2002 418(6896): 387-397.
Yan et al. Yeast Barcoders: a chemogenomic application of a universal donor-strain collection carrying bar-code identifiers. Nat. Meth. (2008) 5(8): 719-725.
Tong et al. Global mapping of the yeast genetic interaction network. Science, 2004, 303:808:813.
Pan X, Yuan DS, Ooi SL, Wang X, Sookhai-Mahadeo S, Meluh P, Boeke JD. dSLAM Analysis of genome-wide genetic interactions in *Saccharomyces cerevisiae*. Methods, Feb. 2007, 41(2):206-221.
Pan X, Ye P, Yuan DS, Wang X, Bader JS, Boeke JD. A DNA integrity network in the yeast *Saccharomyces cerevisiae*. Cell, Mar. 10, 2006 124(5):1069-1081.
Pan X, Yuan DS, Xiang D, Wang X, Sookhai-Mahadeo S, Bader JS, Hieter P, Spencer F, Boeke JD. A robust toolkit for functional profiling of the yeast genome. Mol Cell. Nov. 5, 2004 16(3):487-496.
St Onge et al. (2007) Nat. Genet. 39:199.
Winzeler et al. (1999) Science 285:901.
Brenner (2000) Genome Biol. 1:1.
Kumar et al. (2001) Nature Rev. 2:302.

(Continued)

*Primary Examiner* — Samuel Woolwine
*Assistant Examiner* — Suchira Pande
(74) *Attorney, Agent, or Firm* — Banner & Witcoff, Ltd.

(57) ABSTRACT

Methods of identifying the genotypes of a plurality of single cells, wherein each cell includes a plurality of DNA barcodes, each associated with a genetic mutation or marker, are provided. In particular, methods including linking a plurality of DNA barcodes together to create a stitched barcode, amplifying the stitched barcode and sequencing the stitched barcode are provided. Also provided are methods of determining the presence of at least one genetic mutation in a population of cells.

28 Claims, 16 Drawing Sheets
(8 of 16 Drawing Sheet(s) Filed in Color)

OTHER PUBLICATIONS

Giaver et al. (2004) Proc. Natl. Acad. Sci. USA 101:793.
Eason et al. (2004) Proc. Natl. Acad. Sci. USA 101:11046.
Brenner (2004) Genome Biol. 5:240.
Williams, et al. (Nature Methods Jul. 2006).
Scherens and Goffeau (2004) Genome Biol. 5:229.
Schuldiner et a. (2005) Cell 123:507.
Collins et al. (2006) Genome Biol. 7:R63.
Collins et al. (2007) Nature 446:806.
Tong et al. (2001) Science 294: 2364.
Bader, G. D., Tong, A. H., Shang, L.V., Roth, F. P., Andrews, B. & Boone, C., "Exploiting synthetic genetic interactions to predict pathways and complexes," in Protein-Protein Interactions: A Molecular Cloning Manual (ed. Golemis, E.) (CSHL Press, New York, 2005).
Keogh et al. (2006) Genes Dev. 20:660.
Krogan et al. (2003) Mol. Cell Biol. 23:4207.
Wong et al. (2004) Proc. Natl. Acad. Sci. USA 101:15682.
Wong and Roth (2005) Gentiles 171:829.
Wong et al. (2005) Trends Genet. 21:424.
Zhang et al. (2005) J. Biol. 4:6.
Mani et al. (2008) Proc. Nat. Acad. Sci. USA 105:3461.
Avery and Wasserman (1992) Trends Genet. 8:312.
Zupan et al. (2003) Bioinformatics 19:383.
Demsar et al. (2001) Medinfo 10:956.
Broomfield et al. (2001) Mutat. Res. 486:167.
Schuldiner et al. (2006) Methods 40:344.
Krogan et al. (2006) Nature 440:637.
Collins et al. (2007) Mol. Cell Proteomics 6:439.
Krogan and Greenblatt (2001) Mol. Cell 21:8203.
Krogan et al. (2004) Proc. Natl. Acad. Sci. USA 101:13513.
Keogh et al. (2006) Nature 439:497.
Chowdhury et al. (2005) Mol. Cell 20.801.
Keogh et al. (2005) Cell 123:593.

* cited by examiner

SEQUENCE LISTING

<160> NUMBER OF SEQ ID NOS: 7

<210> SEQ ID NO 1
<211> LENGTH: 18
<212> TYPE: DNA
<213> ORGANISM: Artificial Sequence
<220> FEATURE:
<223> OTHER INFORMATION: Primer binding site

<400> SEQUENCE: 1
gatgtccacg aggtctct                                             18

<210> SEQ ID NO 2
<211> LENGTH: 18
<212> TYPE: DNA
<213> ORGANISM: Artificial Sequence
<220> FEATURE:
<223> OTHER INFORMATION: Primer binding site

<400> SEQUENCE: 2
cgtacgctgc aggtcgac                                             18

<210> SEQ ID NO 3
<211> LENGTH: 18
<212> TYPE: DNA
<213> ORGANISM: Artificial Sequence
<220> FEATURE:
<223> OTHER INFORMATION: Amplification primer

<400> SEQUENCE: 3
agagacctcg tggacatc                                             18

<210> SEQ ID NO 4
<211> LENGTH: 18
<212> TYPE: DNA
<213> ORGANISM: Artificial Sequence
<220> FEATURE:
<223> OTHER INFORMATION: Amplification primer

<400> SEQUENCE: 4
gtcgacctgc agcgtacg                                             18

<210> SEQ ID NO 5
<211> LENGTH: 18
<212> TYPE: DNA
<213> ORGANISM: Artificial Sequence
<220> FEATURE:
<223> OTHER INFORMATION: Amplification primer

<400> SEQUENCE: 5
gtcgacctgc agcgtacg                                             18

<210> SEQ ID NO 6
<211> LENGTH: 19
<212> TYPE: DNA
<213> ORGANISM: Artificial Sequence
<220> FEATURE:
<223> OTHER INFORMATION: Sequence tag

```
<400> SEQUENCE: 6
gctgtcgtcg ctactatta                                          19

<210> SEQ ID NO 7
<211> LENGTH: 19
<212> TYPE: DNA
<213> ORGANISM: Artificial Sequence
<220> FEATURE:
<223> OTHER INFORMATION: Sequence tag

<400> SEQUENCE: 7
taatagtagc gacgacagc                                          19
```

METHODS AND APPLICATIONS FOR STITCHED DNA BARCODES

RELATED APPLICATIONS

This application claims priority from U.S. provisional patent application Nos. 60/975,354, filed Sep. 26, 2007 and 61/049,134, filed Apr. 30, 2008, each of which is hereby incorporated herein by reference in its entireties for all purposes.

STATEMENT OF GOVERNMENT INTERESTS

This invention was made with government support under National Institutes of Health grant number HG003224. The Government has certain rights in the invention.

BACKGROUND

Physical and functional interactions between gene products can be uncovered through classical genetic screens and through high throughput genetic screens involving mutations or deletions of one or more genes. In standard genetic screen experiments, a gene is mutated or deleted and the resulting phenotype is assessed. High throughput genetic screens rely on the screening of hundreds, thousands or more mutants simultaneously for phenotypes of interest.

Libraries of strains, each deleted for any one of several thousand genes, are known in the art. For example, the *Saccharomyces* Genome Project has revealed the presence of more than 6000 open reading frames (ORFs) in the *S. cerevisiae* genome. Many of these genes have been disrupted and replaced with the KanMX (KAN) cassette, which confers resistance to the antibiotic G418 (GENETICIN®). (See *Saccharomyces* Genome Deletion Project, Stanford University, sequence.stanford.edu/group/yeast_deletion_project.deletion3.html). Libraries can be made using any suitable markers for selection known in the art. For example, the markers may confer resistance to the antibiotics hygromycin B (HygR), nourseothricin (NatR) and bialaphos (PAT). Often the markers NatMX (NAT) and KanMX (KAN) are used. NAT and KAN-marked deletion strains can be obtained by any suitable method known in the art. For example, the strains may be pre-existing or may be constructed de novo a variety of methods. For an example of single- and double-mutant strain construction see Daniel J A, Yoo J, Bettinger B T, Amberg D C, Burke D J. Eliminating gene conversion improves high-throughput genetics in *Saccharomyces cerevisiae*. *Genetics*, 2006 January, 172(1):709-711.

The yeast knockout (YKO) library contains specific "molecular barcodes" referred to as "uptags" and "downtags." These are short (typically 20 base pair) DNA sequences placed within the genome of each deletion strain adjacent to the deletion locus. Each barcode sequence is associated with only one deletion locus, and the sequence can be used to reveal which gene has been deleted within a particular cell. Uptags are flanked by the same pair of sequences, permitting the multiplex amplification of all uptags using a single PCR primer pair. Similarly, downtags are flanked by the same pair of sequences (which differ from the pair of sequences flanking the uptag barcodes), permitting the multiplex amplification of all downtags using a single PCR primer pair. Microarray technology has been used in conjunction with these barcodes to assist in the identification of large numbers of mutants and their respective phenotypes (e.g., relative growth rate under a particular growth condition) (For example, see Giaever G et al. Functional profiling of the *Saccharomyces cerevisiae* genome. *Nature*, 2002 Jul. 25, 418(6896):387-391). In this approach, a population of barcoded deletion strains are mixed and grown under selective conditions; a multiplex amplification of barcodes is performed for cells both pre- and post-selection; amplified barcodes from pre- and post-selection are obtained and distinguishably labeled; a microarray displaying sequences complementary to barcode sequences is then used to quantify the relative abundance of barcodes and thus the effect of selection on the relative abundance of each strain type. Other methods known in the art can be used to produce arbitrarily large collections of yeast strains that each carry a unique DNA barcode sequence. A given genomic alteration carried by such a bar-coded strain may thus be uniquely identified. See Yan et al. Yeast Barcoders: a chemogenomic application of a universal donor-strain collection carrying bar-code identifiers. *Nat. Meth.* (2008) 5(8): 719-725.

One high-throughput method of uncovering genetic interactions is the synthetic genetic array (SGA) analysis method. This selection involves the mating of one mutant strain carrying a particular marker to an entire library of yeast deletion strains carrying a second marker to generate diploid strains which are heterozygous at two different loci for two different mutations of interest. Heterozygous diploid strains can then be sporulated, and haploid double mutants are specifically recovered after sporulation by virtue of independently selectable markers linked to each of the mutations of interest, by virtue of a selectable marker gene that is specifically expressed in haploids of a particular mating type, and by virtue of one or more negatively selectable markers that are necessarily present in all diploid cells but not in all haploid cells. The effect of having both mutations on yeast cell survival is then determined by measuring the size of the yeast colonies grown on a plate. The growth of these strains provides an indication of the degree of interaction of the combined effect of the two mutant strains on yeast cell growth. Growth of the colonies is quantified by photographing the plates containing the yeast and measuring the size of the colonies. See Tong et al. Global mapping of the yeast genetic interaction network. *Science*, 2004, 303:808:813.

A related high throughput genetic screen used to probe genome-wide genetic interactions is called dSLAM, (diploid-based synthetic lethality analysis on microarrays) (See Pan X, Yuan D S, Ooi S L, Wang X, Sookhai-Mahadeo S, Meluh P, Boeke J D. dSLAM analysis of genome-wide genetic interactions in *Saccharomyces cerevisiae*. *Methods*, 2007 February, 41(2):206-221; Pan X, Ye P, Yuan D S, Wang X, Bader J S, Boeke J D. A DNA integrity network in the yeast *Saccharomyces cerevisiae*. *Cell*, 2006 Mar. 10, 124(5):1069-1081; Pan X, Yuan D S, Xiang D, Wang X, Sookhai-Mahadeo S, Bader J S, Hieter P, Spencer F, Boeke J D. A robust toolkit for functional profiling of the yeast genome. *Mol Cell*. 2004 Nov. 5, 16(3):487-496.). In dSLAM, the relative growth rate of mutant yeast strains grown in competition is measured using molecular barcodes and microarray detection. The process relies on creating a population of double mutant strains via en masse transformation of a knockout cassette targeting a particular gene of interest into a library of heterozygote diploid yeast knockout strains. Each double mutant contains the mutation of a particular gene of interest (the 'query allele') in combination with a mutant from the library ('the array allele'). Once this strain pool is created, it is then sporulated and grown on selective media to obtain the corresponding population of haploid double-mutant cells (haploid selection is essentially as described above for SGA). The population of haploid double-mutant cells is then placed under selective growth conditions to determine if the combination mutant has selective growth advantages or disadvantages compared to the single mutant or wild-type. After sporulation and selection, genomic DNA is prepared and the molecular barcodes are PCR amplified in the presence of labeled primers. The DNA derived from the double mutants can be amplified in the presence of Cy3 and the DNA from the control (single mutants) can be amplified in the presence of Cy5. Subsequent analysis using microarrays displaying oligos complementary to barcodes is used to decipher the relative abundance of yeast cells containing double mutants versus the abundance of yeast cells containing single mutants. Unfortunately, the dSLAM method is limited in that every strain in the population under study must share a particular mutation or 'query allele' of interest.

Despite the large scale successes of recent breakthroughs in high-throughput screening and selection, there remains a need in the art for techniques which allow screening of even larger numbers of combination mutants and faster and less expensive methods to perform such screens. It would be advantageous to have a method of high-throughput screening that can be used in combination with DNA barcoding technology in which multiple barcode sequences contained at non-adjacent or unlinked loci within a single cell can be fused to generate 'stitched barcodes' such that each stitched barcode uniquely identifies a particular combination of distinct genetic alterations.

SUMMARY

Significant scientific and medical interest exists for screening for phenotypes in mutants in organisms carrying more than one mutation, for example, describing the presence or absence of complementation and/or degree of interaction between mutant alleles. The present invention is based in part on the discovery of a method of high-throughput screening and selection utilizing a stitched barcode technology. Accordingly, in certain exemplary embodiments, a method of determining the presence of at least one genetic mutation in a population of organisms (e.g., cells) is provided. The method includes creating one or more aqueous emulsion droplets, wherein at least one emulsion droplet includes an organism having at least one barcode-associated (i.e., "barcoded") mutation, performing a polymerase chain reaction (PCR) in the emulsion droplet to amplify at least one barcoded mutation, recovering the aqueous phase from the emulsion droplet, wherein the aqueous phase includes the amplified, barcoded mutation, and detecting the presence of the amplified, barcoded mutation. In certain aspects, the organisms are *S. cerevisiae*. In certain aspects, the barcoded mutation and/or the organism include a detectable label. In other aspects, the emulsion droplet is a water-in-oil or a water-in-oil-in-water emulsion droplet. In certain aspects, the amplified, barcoded mutation is genetic deletion or a genetic insertion (e.g., an insertion present on a plasmid). In certain aspects, a population of organisms includes at least 1, 10, 100, 1000, 10,000, 100,000, 1,000,000 or more different barcoded mutations. In certain aspects, for at least 50%, 55%, 60%, 65%, 70%, 75%, 80%, 85%, 90%, 91%, 92%, 93%, 94%, 95%, 96%, 97%, 98%, 99% or 100% of the organisms, each contains at least 1, 2, 3, 4, 5, 10, 20, 30, 40, 50, 100, 1000, 10,000, 100,000, 1,000,000 or more barcoded mutations.

In certain exemplary embodiments, a method of identifying the genotype of an organism, wherein the organism comprises a plurality of barcoded mutations is provided. The method includes the steps of linking a plurality of barcoded mutations together to create a stitched barcode, amplifying the stitched barcode, and determining the identity of the stitched barcode. In certain aspects, the step of determining the identity is performed by detecting the presence of at least one detectable label in the stitched barcode. In certain aspects, each barcoded mutation includes a detectable label. In other aspects, the organism is *S. cerevisiae*. In certain aspects, the plurality of barcode-associated mutations includes at least one vector that expresses a gene encoding at an RNA that is capable of inhibiting expression an endogenous gene. In other aspects, the organism is a mammal, e.g., *H. sapiens* and the step of determining is performed on a cell derived from said mammal, e.g., *H. sapiens*.

In certain exemplary embodiments, a method of making a knockout library, e.g., an *S. cerevisiae* knockout library, is provided. The method includes the steps of providing a first population of organisms each of which contains at least one of a first plurality of barcodes, providing a second population of organisms each of which contains at least one of a second plurality of barcodes, and combining the first population of organisms and the second population of organisms such that at least one resulting organism comprises a combination of at least one of the first plurality of barcodes and at least one of the second plurality of barcodes. In certain aspects, the method includes the step of selecting the at least one resulting organism comprising a combination of at least one of the first plurality of barcode-associated mutations and at least one of the second plurality of barcode-associated mutations. In other aspects, the method includes the step of subjecting the at least one resulting organism comprising a combination of at least one of the first plurality of barcode-associated mutations and at least one of the second plurality of barcode-associated mutations to a selection that alters the relative abundance of organisms within the library in a manner that is dependent upon at least one phenotype of at least one combination of barcode-associated mutations. In yet other aspects, the method includes the step of determining relative abundance of organisms of each population of one or more of the steps described above by sequencing linked barcodes from a cell derived from one or more of the steps. In certain aspects, the first population of organisms and the second population of organisms are combined by mating.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

DETAILED DESCRIPTION

Figure 1:
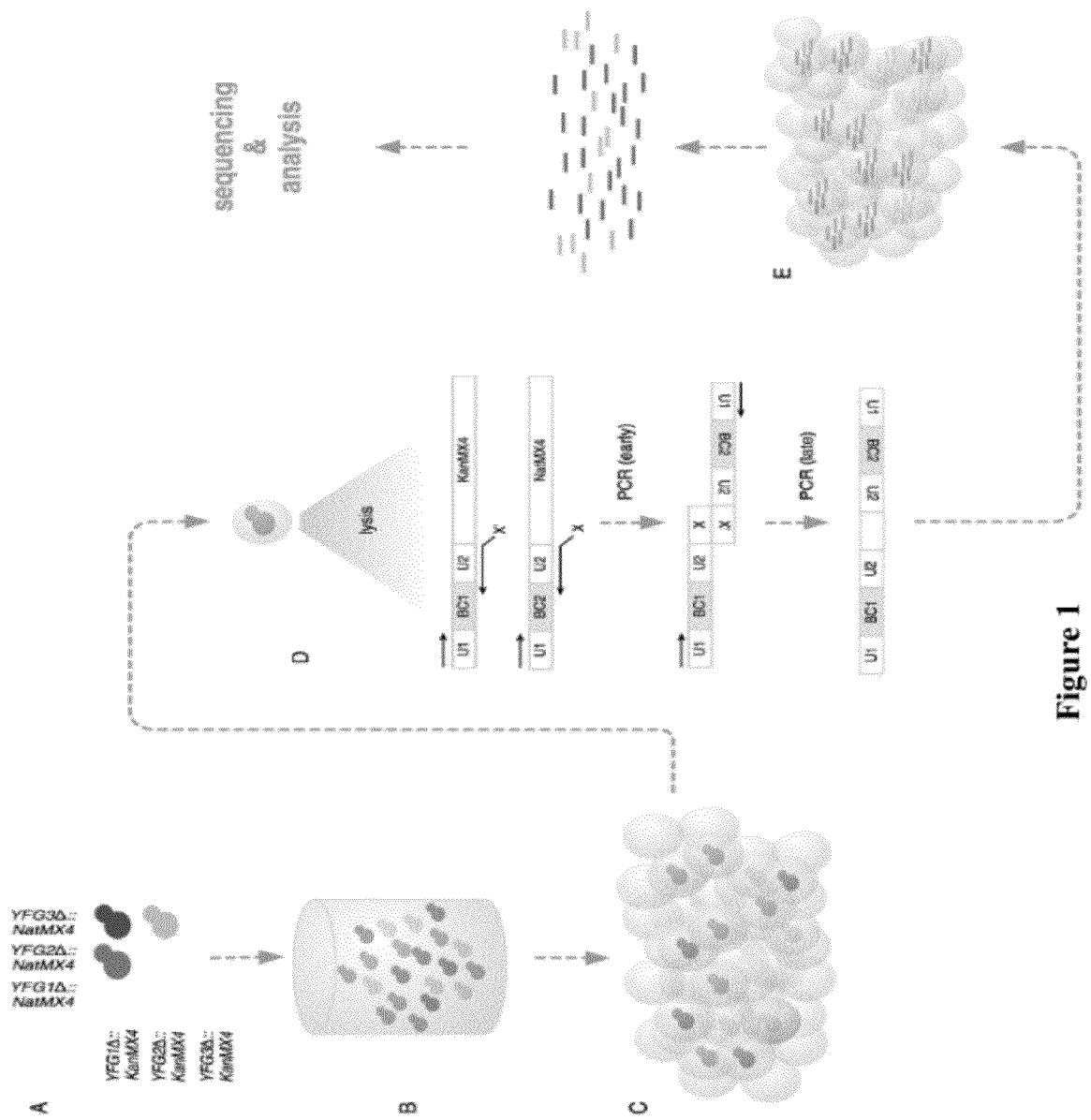
FIGS. 1A-1E schematically depict an overview of the barcode fusion genetics (BFG) strategy for genetic interaction mapping. (A) A complex pool of double mutant strains is efficiently generated from single mutant strain pools by crossing a pool of $Kan^R$ deletion strains with a pool of $Nat^R$ deletion strains using the previously-developed SGA approach. (B) Strains in the double mutant pool are grown competitively, such that faster growing strains represent a greater fraction of the final population. (C) A dilute suspension of double mutant cells is used to generate a water-in-oil emulsion, such that each aqueous droplet contains either zero or one cell encapsulated together with PCR reagents. This step is necessary to ensure that each barcode fusion represents a single double mutant cell. (D) a fusion PCR reaction (also known as 'crossover PCR' or 'overlap-extension PCR') is carried out within the emulsion to 'stitch' together barcode (BC) sequences from two distinct loci to form a composite barcode. Each composite barcode thus uniquely identifies a double mutant strain. (E) The abundance of each composite barcode (and thus, the abundance of its corresponding double mutant strain) is measured via 'next generation' sequencing at a current cost of approximately $1500 per five million barcodes. Genetic interactions are then inferred by measured double mutant strain abundance that deviates from expectation.

It would be useful if a throughput approach were to allow the relative quantification of the relative abundance of double mutant strains within a heterogeneous population that is not subject to limitations of current screening methods. For example, one might wish to assess the relative abundance of a population of cells containing all pair-wise combinations of a given set of mutations (which might include insertions, deletions, or other modifications). Accordingly, in certain exemplary embodiments, methods and compositions for using molecular barcodes to identify various combinations of mutations or deletions within a cell are provided. As used herein, the term "barcode" refers to a unique DNA sequence that can be used to flank one or both ends of each deletion or genetic alteration, in an organism, e.g., yeast. The terms "barcoded mutation" and "barcode-associated mutation" as used herein, refer to a deletion or genetic alteration flanked on one or both ends by a barcode. The term "stitched barcode" may refer to many DNA sequences, or many barcodes, representing many genetic alterations, for example, when numerous barcodes are linked together. Barcode assays are particularly useful for determining the genetic basis of drug sensitivity and resistance. Barcode technologies are known in the art (see Winzeler et al. (1999) *Science* 285:901; Brenner (2000) *Genome Biol.* 1:1; Kumar et al. (2001) *Nature Rev.* 2:302; Giaever et al. (2004) *Proc. Natl. Acad. Sci. USA* 101:793; Eason et al. (2004) *Proc. Natl. Acad. Sci. USA* 101:11046; and Brenner (2004) *Genome Biol.* 5:240).

The use of barcodes for screening fitness in mutants is not limited to strains or organisms having engineered barcodes marking null (e.g., deletion) or other mutant alleles only. Unique DNA barcodes can be incorporated by those skilled in the art into genetic vectors of various origin for the purpose of identifying the presence of a vector in a pool of engineered strains. Similarly, pairs of barcodes can be used in pools of strains to identify which strains carry a given pair of engineered genetic vectors. Engineered, genetic vectors are routinely used to screen for interactions in complementation assays such as yeast two-hybrid to identify pairs of protein fragments that interact (See Walhout et al. High-throughput yeast two-hybrid assays for large-scale protein interaction mapping. *Methods* (2001) 24(3):297-306). Measurements of relative abundance (thereby measuring relative growth rates) for strains carrying other combinations of alterations can also be informative. For example, the combination of a mutant allele at one locus with an engineered gene expressed at high levels at a second locus can be used, for example, to understand kinase-substrate relationships (See, for example, Sopko et al. (2008) *Mol. Biosyst.* September, 4(9):920-933. Epub 2008 Jul. 17) and literature on synthetic dosage lethality interactions discussed therein).

As used herein, the term "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., *Danio Rerio*) a roundworm (e.g., *C. elegans*) and any transgenic species thereof. The term "organism" further includes, but is not limited to, a yeast (e.g., *S. cerevisiae*) cell, a yeast tetrad, a yeast colony, a bacterium, a bacterial colony, a virion, virosome, virus-like particle and/or cultures thereof, and the like.

Barcode assays may be used to identify mutations, deletions, or genetic alterations present within cells. For example, each genetic deletion within the yeast knockout library is associated with a particular specific barcode. This genetic deletion is engineered to contain a particular DNA sequence that corresponds to the particular gene that was deleted. This is helpful for high throughput screening applications where many mixed populations contain numerous genetic alterations. The use of many molecular barcodes allows a researcher to rapidly identify the particular genetic mutations that are identified in a screen.

Identification of molecular barcodes, for example, may occur via PCR amplification followed by sequencing to determine the DNA sequence of the barcode which refers to a particular mutation. Barcodes may also be labeled and applied to a microarray. Using detectable labels (e.g., different color labels) allows one to quantitatively determine the presence or absence of various particular barcodes, referring to particular genetic mutations, or deletions, in a large heterogeneous population.

In certain exemplary embodiments, a variety of genetic screens or high-throughput (HT) screening applications are provided. Temperature sensitivity screens, growth assays, drug resistance selections, colony size measurements, reporter gene assays or any type of selection or screening scheme will be applicable to the disclosed methods.

Figure 5:
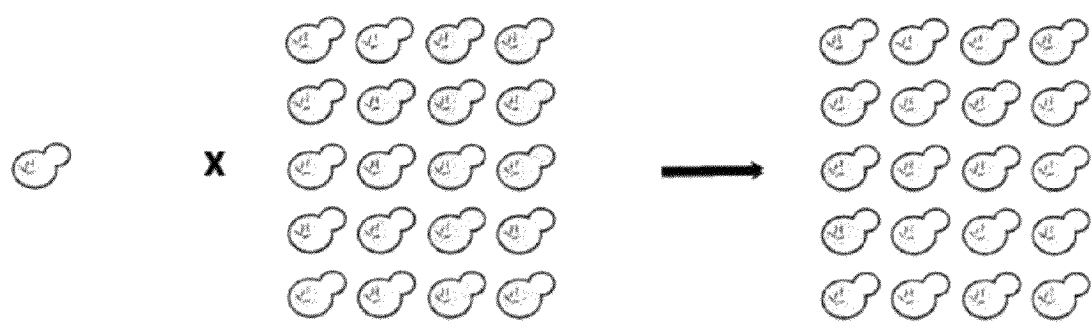
FIG. 5 schematically depicts the 'one-by-many' approach to high-throughput (HT) genetic interaction screens.
Figure 7:
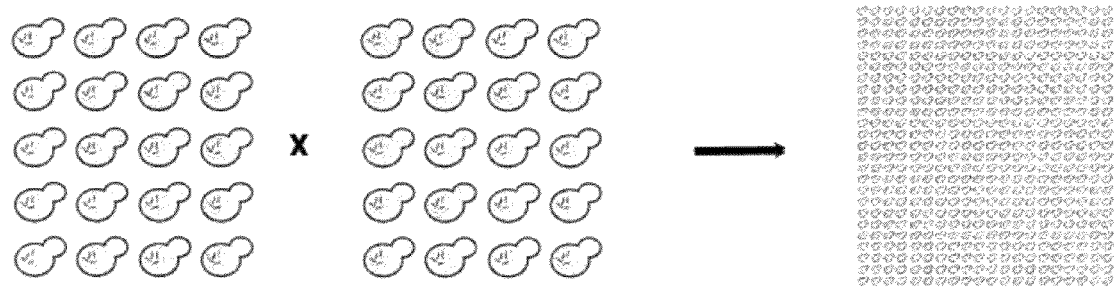
FIG. 7 schematically depicts the 'many-by-many' approach of HT genetic interaction screens.

A critical component of a genetic screen or high-throughput screening application is the particular genotype of the strains being studied. As discussed above, current methods of screening rely the "one-by-many" approach (FIG. 5), where one particular mutation (e.g., yfg1Δ) is combined with a library of various mutants/deletions either by mating or by transformation (e.g., using a yfg1 deletion cassette). Applying the molecular barcode technology to these screens limits a researcher to one barcode representing one mutation, commonly the mutation within the library. In this sense, the barcode simply tells one what gene has been identified from the library. If a library were to be used that comprises strains with multiple deletions or various combinations of deletions or alterations, it would become labor intensive to determine the identity of the cells. This especially becomes problematic when a large scale "many-by-many" selection approach (FIG. 7) is used. Using standard technology, one amplification reaction would be required for each DNA barcode.

It would be advantageous to use the barcoding technology for genotype identification where the genotypes of the starting strains contain more alterations, mutations, or deletions than what is available with the current methods. It is also advantageous for barcodes to represent RNAi vectors, shRNAs, reporter plasmids, or any other engineered feature commonly used in molecular genetic applications. For example, if a strain contains two or more genetic deletions, a barcode needs to be associated with each deletion and it would be advantageous to identify each barcode in a single reaction. Standard barcoding applications would require one or more separate PCR reactions for each strain and subsequent sequencing to identify two or more genetic deletions within a strain. This is costly and inefficient.

One aspect of the invention relates to "stitching" one or more DNA barcodes together in a single reaction which allows the stitched barcode to be identified by one sequencing reaction. As used herein, the term "stitching" refers to the linking of a plurality of molecular barcodes, for example, via an amplification reaction such as barcode crossover PCR, or an extension reaction.

Figure 13:
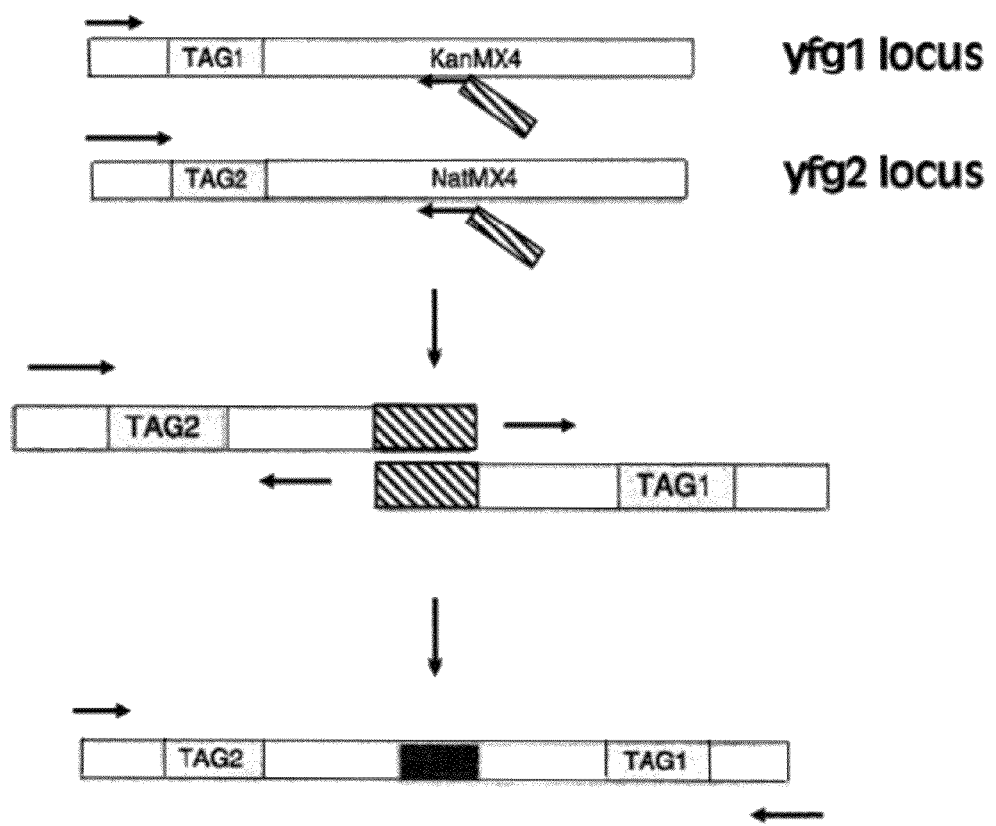
FIG. 13 schematically depicts the method of one-step overlap extension PCR to 'stitch' DNA barcodes in double deletion yeast strains.
Figure 14:
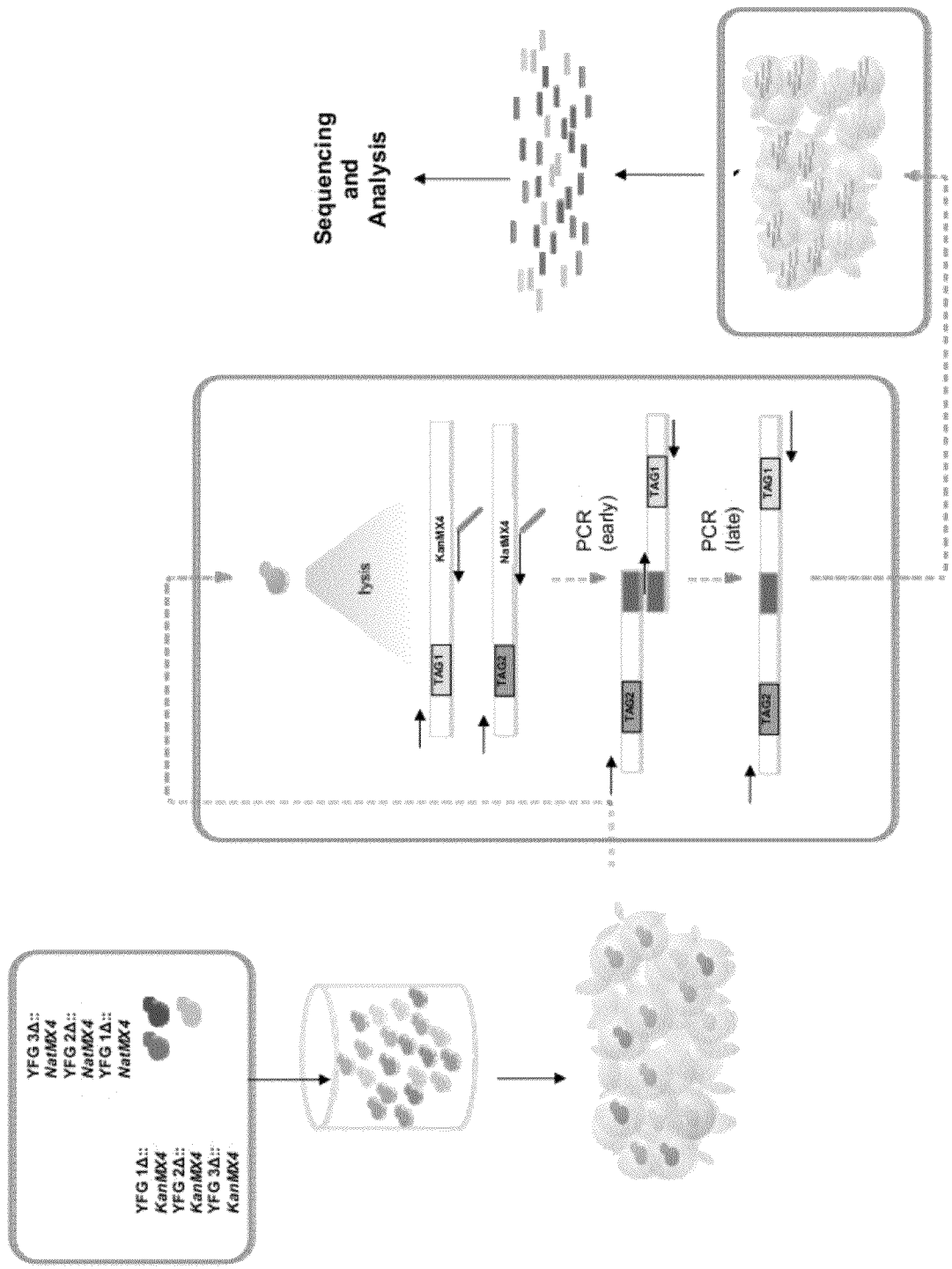
FIG. 14 schematically depicts a method for obtaining stitched barcode tags with emulsion PCR according to certain exemplary embodiments.

For example, FIGS. 13 and 14 show two molecular barcodes, referred to in the Figure as TAG1 and TAG2. In one aspect, these barcodes are located on separate chromosomes and correspond to two separate genetic deletions, for example, yfg1Δ and yfg2Δ. A set of primers is used to extend, or amplify one particular tag, such as TAG2, and another set is used to amplify the sequence containing the other tag, TAG1. Two of the primers used to amplify the two tag sequences have an additional, specific 5' sequence (overlap sequence) which permits 5' complementarity between the primers, and is incorporated via a PCR reaction of the corresponding tags. Thus, after extension an overlapping 3' homologous region is introduced (the specific common region) into the sequences of the tags allowing them to hybridize with one another, as shown in FIGS. 13 and 14. At this stage, only the specific common region is hybridizing. Next, an extension reaction occurs to create a DNA template containing both TAG1 and TAG2. Primer sequences specific to the entire template can then be used to amplify the entire molecular barcode containing TAG1 and TAG2. This barcode may be sequenced to identify TAG1 and TAG2 and to associate these barcodes with their related genetic alteration. Sequencing reactions such as the dideoxy or the Sanger method are well known to one of skill in the art and may be employed to identify the molecular barcodes of the present invention. It is advantageous to "stitch" or link or associate two or more barcodes together, rather than working with separate barcodes, as would be required by previous methods of identifying molecular barcodes.

In an additional aspect of the invention, a genetic screen is carried out where a large heterogenous population of cells is screened or selected via any well known method of screening or selection. This heterogenous population may contain multiple alterations, or deletions, each of which are represented via barcodes. Ensuring that each multiply-altered strain in a large population carries a unique barcode is problematic. Performing numerous PCRs in this type of population may lead to generation of a barcode that is not unique to a single cell. The barcode may erroneously include a combination of barcodes from various cells within the population and may not represent the combination of barcodes actually present within a single cell.

To remedy this problem, the PCR amplification of barcodes may be accomplished by carrying out the PCR amplification within an emulsion of aqueous and hydrophobic phases. Emulsion droplets form a separate microreaction chamber for clonal PCR, with each droplet typically containing no more than one cell. The average size of emulsion droplets containing cells is between 5 and 20 microns.

In one embodiment, cells are grown to suitable density and pooled in preparation for emulsion, and kept at 4° C. Typical haploid yeast culture densities represented by measurements of 0.1-1.0 (OD600 in YPD) correspond (on average) to $10^6$ to $10^7$ cells per mL. Concentration estimates of aqueous compartments capable of encapsulating a cell ("capable compartments") in emulsions of the type described here range from $10^8$-$10^9$ per mL. A 1% average occupancy rate of capable compartments by cells is sufficient to ensure with high probability that any given compartment contains at most one cell. (Using the lower limit of $10^8$ as the estimated number of aqueous compartments, if $10^6$ cells are emulsified independently then the probability (Poisson, lambda=0.01, x>=2) that any single compartment contains more than one yeast cell is $5 \times 10^{-5}$). To limit aggregation and favor the independent assortment of cells in the emulsion, the aqueous mixture is subjected to vortexing and/or brief sonication. Higher than normal concentrations of PCR buffer (NEB Taq Buffer, 1.5×) and dNTPs (0.5 mM each) are used to boost PCR yield. The suspension of yeast cells and PCR reagents are then emulsified, e.g., by using an adaptation of the process described by Williams, et al. (*Nature Methods* July 2006). Surfactants, e.g., Triton X-100 (Sigma) (0.05% by volume) and ABIL EM 90 (Degussa) (2% by volume) are dissolved in molecular biology grade mineral oil (Sigma) and this mixture is kept ice-cold (4° C.). The ice-cold aqueous mixture of cells and PCR reagents is added dropwise to the oil mixture in a volume ratio of 1:9 over two minutes with magnetic stirring in a 1 mL cryovial (Corning) at 1400 r.p.m. with a 3×8 cylindrical stir bar with pivot point (VWR). The mixture is stirred for additional 5 minutes and then aliquoted in 0.2 mL quantities into five 0.5 mL thin-walled PCR tubes for thermal cycling.

Figure 15:
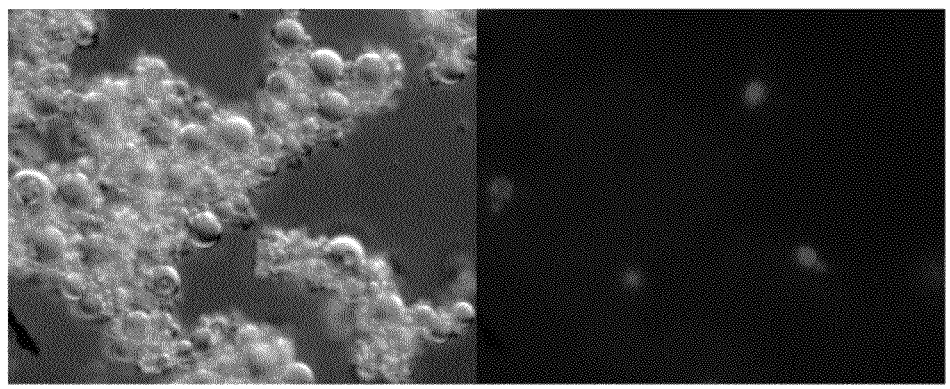
FIG. 15 depicts single yeast cells encapsulated in aqueous droplets within a water-in-oil emulsion (top panel) and cells within water-in-oil emulsion droplets with cell growth of one to two doublings allowed after encapsulation (bottom panel).
Figure 15:
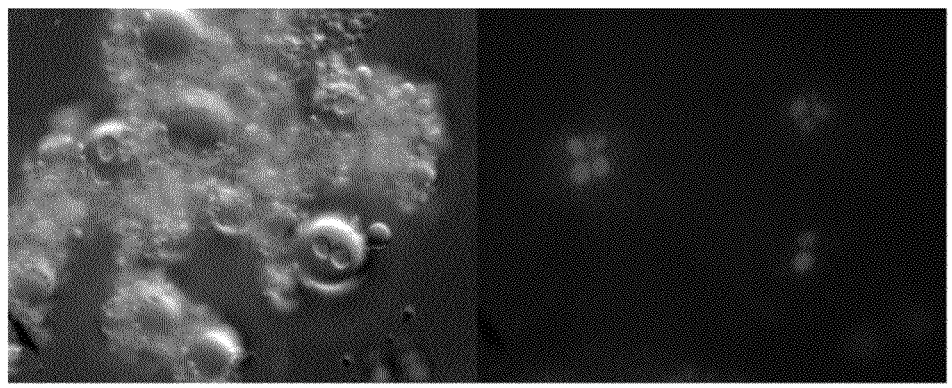

FIG. 15 shows a photograph depicting a water-in-oil emulsion of yeast cells. This figure illustrates that, primarily, one yeast cell was contained within an emulsion droplet. The emulsion droplet provided a chamber to perform PCR amplification of the barcodes without the contamination of DNA from other cells (See FIG. 16).

In certain exemplary embodiments, an aqueous suspension of selected yeast cells is mixed with oil to create an emulsion, wherein a majority of aqueous droplets in the emulsion are comprised of at most one yeast cell in addition to arbitrary concentrations of other aqueous reagents. In certain exemplary embodiments, using water-in-oil emulsions to isolate strains has the following scale: at least $10^8$ aqueous droplets/mL of emulsion corresponds to at least at least $10^6$ cells/mL to serve as template for PCR amplification.

The yeast cell may be lysed within the droplet, for example, via enzymatic means such as, e.g., using a β-1,3-glucan laminaripentaohydrolase and/or a β-1,3-glucanase (e.g. Zymolyase™, Zymo Research Corp.) Zymolyase may be added to the oil and water before the droplet is formed or after. Lysing the cell within the droplet ensures that a particular cell's genomic contents are kept within the droplet. A period of heating is also sufficient for lysis (He et al. (2005) *J. Rapid Meth. Auto. Microbiol.* 13:19).

The emulsion droplet is stable under repeated thermal cycling to temperatures as high as 95° C. Yeast cells will lyse at upon heating, e.g., 2 minutes or more at 95° C. A PCR program is used which holds at 95° C. for 12 minutes prior to the first round of primer annealing. Additional lysis agents (for example, recombinant zymolyase or lyticase proteins derived from *Oerskovia* or *Arthrobacter*) may in principle be added to improve lysis efficiency. After lysis, the reagents necessary for PCR are added to the emulsion and then exposed to conditions allowing the amplification reaction to proceed. The PCR reagents are added directly to the aqueous solution containing a known concentration of yeast cells. DNA polymerase (Taq Polymerase, NEB) buffer and dNTPs are used in slightly higher than normal concentrations (1.5× and 0.5 mM, respectively) compared with manufacturer specifications. Also, the use of bovine serum albumin (noted in Williams et al. (2006) *Nature Methods* 3:545) is advantageous to reduce or prevent sequestration of the DNA polymerase on the surface of the emulsion droplet. These conditions routinely include a denaturing step, a primer annealing step, and a primer extension step. A barcode crossover PCR may be allowed to proceed in order to "stitch," link, combine and/or associate the barcodes together, as discussed above. The stitching may, for example, include a primer extension reaction, which incorporates an overlap sequence into the barcode-containing amplicon. This common region then is allowed to hybridize with another barcode creating a stitched barcode, which can consist of 2, 3, 4, 5, 6, or more barcodes. Finally, the stitched barcode may be amplified until adequate amounts of DNA are amplified. The emulsion is centrifuged and subjected to aqueous extraction in ethyl ether and ethyl acetate, and the aqueous component is cleaned up with a Qiagen miniprep kit. The DNA may then be sequenced.

Any suitable strain of yeast and any suitable plasmid can be used to create the yeast strains used in the embodiments. (See e.g., Baudin et al. (1993) *Nucleic Acids Res.* 21: 3329; Wach et al. (1994) *Yeast* 10:1793).

In a further embodiment, the screening methods can be applied to other barcode-associated perturbations and organisms. For example, barcodes can be used to identify cells that have been treated with a specific RNAi reagent (e.g., siRNAs or shRNAs), overexpression constructs, or antisense nucleic acid to alter expression of a protein.

In addition, the approach can be applied to produce a stitched barcode that identifies perturbations of different types of treatments and in different combinations. For example, the approach can be used to detect the presence of the combination of a specific RNAi, a specific overexpression construct, and a specific gene deletion.

The approach may be used in cells derived from any suitable species. Other species that can be used include mammals such as rats, mice, non-human primates, and humans. The species may also be zebrafish (*Danio rerio*) or the nematode, *C. elegans*. The cells may be of any suitable type; for example, primary cells, or cells that have been immortalized or have become cancerous spontaneously. Cells derive from knock-out and knock-in versions of these species may also be used. Techniques for developing knock-out and knock-in mice are well-developed in the art.

In a further embodiment, the relative abundance of combinations of sequence variants can be determined. PCR primer pairs that are complementary to a genetically altered sequence are used such that amplification only takes place for one of the sequence variants at each locus ('variant-selective primer pairs'). If multiple SNPs were segregating within a population, a corresponding set of variant-selective primer pairs could be used to perform PCR within an emulsion carrying a dilute cell suspension. A primer may be introduced which carries a barcode and a nucleic acid region specific for the variant. The primer is designed to be incorporated within a barcode crossover PCR. In this way, a stitched barcode can be produced that identifies a combination of variants arising from a given cell. Such a barcode may be used to estimate relative abundance of each combination of these variants within a heterogeneous population. Such an approach can be used, for example, in cancer cells that may contain variants of particular nucleic acid sequences. The cancer cells can be obtained from a variety of sources. Cells of cancer cell lines well-known in the art may be used; for example, COS, HeLa, NRK, HL60, Raji, Ramos. Cancers cells may also be obtained from tumors.

In a further embodiment, methods of screening for drug targets can be performed (See Ooi et al. (2006) *Trends Genet.* 22:56). Yeast have been demonstrated to be a useful model organism for investigating drug mechanism of action and for establishing cell-based functional assays for use in high-throughput screening. Genetic interactions (e.g., when two or more genes contribute jointly to a phenotype) in yeast have been shown to be useful in the characterization of biological functions relevant to human disease. Screening of genetic interactions and their dependence on various environmental factors such as drug treatment can be performed. In certain exemplary embodiments, epistatic interactions (e.g., when the action of one gene is modified by one or several other genes) will be identified. In certain exemplary embodiments, epistatic interactions (affecting phenotypes (such as growth) will be surprising given one or more models of what is expected by one of skill in the art (see, e.g., Mani et al. (2008) *Proc. Nat. Acad. Sci. USA* 105:3461). Identification of one or more genetic interactions can aid in the elucidation of genetic complexity as many traits and/or functions are encoded by many (e.g., 2, 3, 4, 5, 6, 7, 8, 9, 10, 20, 30, 40, 50, 60, 70, 80, 90, 100, 1000, 2000, 3000 or more) gene products. For example, the identification of genetic interactions can allow one to identify how genes act in combination or tandem to control certain phenotypes, i.e., the identification of gene function.

A variety of suitable genetic screens may be used to identify genetic interactions using methods such as, for example, synthetic genetic array (SGA) technology (described in Tong et al. (2004) *Science* 303:808), the diploid-based synthetic lethal by microarray (dSLAM) technique (described in Pan et al. (2004) *Mol. Cell.* 16:487), the epistatic mini-array profile technique (eMAP) (described in Collins et al. (2006) *Genome Biol.* 7:R63) and the like. Certain suitable screens are discussed further herein.

As in the other embodiments, using the approach to assess the effects of drugs is not restricted to gene deletions in the yeast strains. Other alterations to the strains can include overexpression alleles of wild-type or mutated genes of interest, temperature-sensitive alleles, for example. In certain exemplary embodiments, a barcode is associated with each alteration within a cell.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures and accompanying claims.

Example 1

Many-by-Many Mating of Yeast Strains Having Deletions

Figure 9:
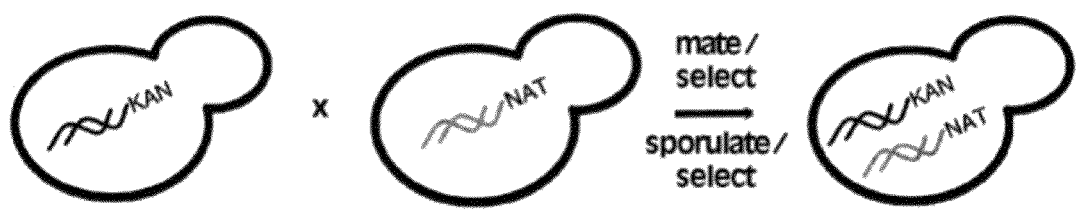
FIG. 9 schematically depicts the use of two yeast deletion strains with unique barcode sequences according to certain exemplary embodiments.
Figure 10:
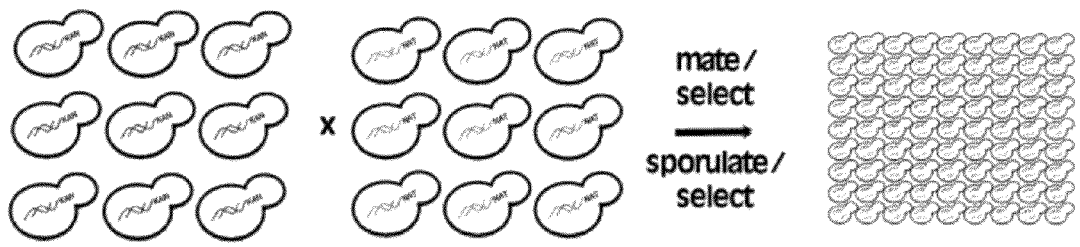
FIG. 10 schematically depicts the use of many yeast deletion strains with unique barcode sequences according to certain exemplary embodiments.

Yeast strains harboring deletions may be mated in a many-to-many format to identify functional gene interaction. Two separate yeast libraries each having numerous genes deleted and replaced with a molecular barcode-tagged marker are mated. One library contains strains resistant to kanamycin (KAN), and the second contains strains resistant to nourseothricin (NAT). Mated yeast having copies of genes from both libraries are then selected based on resistance to both KAN and NAT (FIGS. 9 and 10). The resulting yeast cells contain both selectable markers and now have a unique combination of mutants/deletions, one from the KAN library and the other from the NAT library. The resulting cells may be sporulated if the haploid version of the mutant is desired.

A selection scheme, such as growth at an elevated temperature, for example, may be employed to select for a particular combination of genetic mutants (one from each library) that has the ability to grow better at the elevated temperature. Once the selection is complete, the identity of a combination of genetic mutations surviving the selection is determined by stitching the barcodes together and sequencing the stitched barcode. Genetic mutations failing to survive the selection may be identified if the corresponding barcodes are present prior to the selection but absent after the selection.

Figure 11:
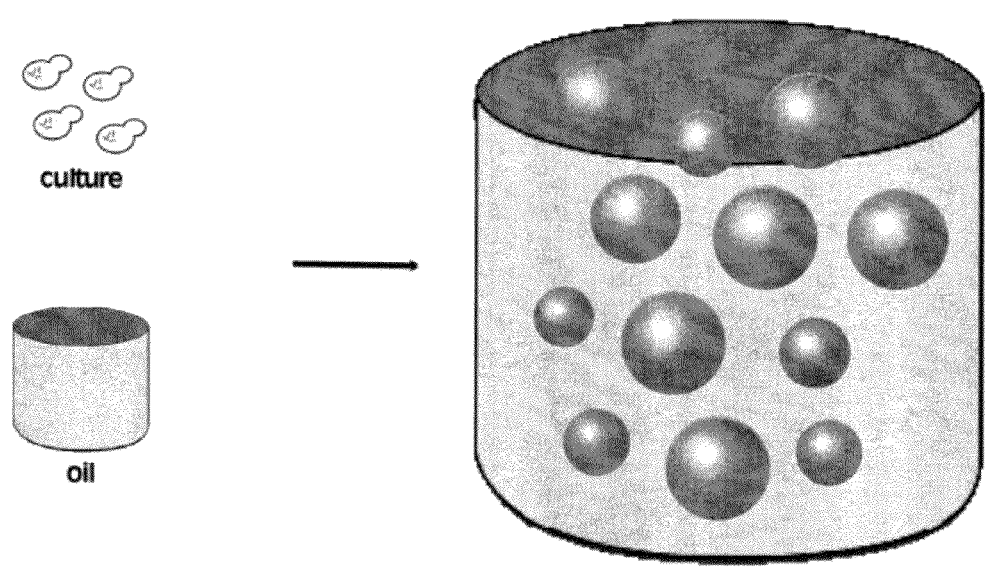
FIG. 11 schematically depicts the use of water-in-oil emulsions to isolate yeast strains.
Figure 12:
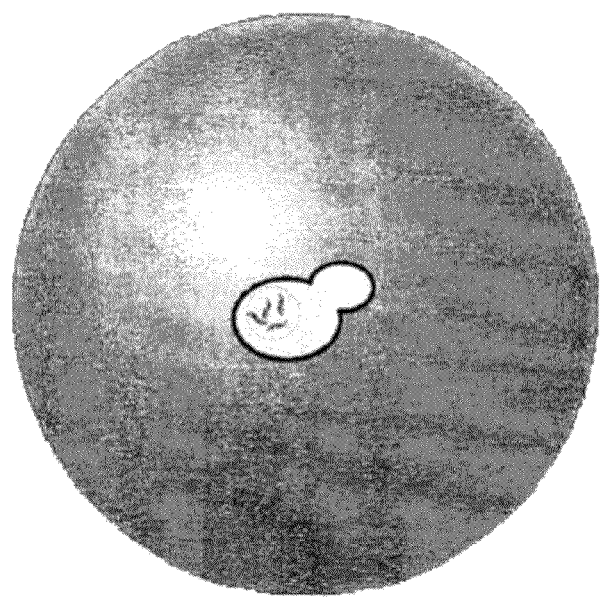
FIG. 12 schematically depicts a single yeast cell in an aqueous droplet within a water-in-oil emulsion. Once a yeast cell is in an aqueous droplet, its identity can be uniquely encoded by combining barcodes that each individually identify a single altered locus.

To identify the stitched barcode, the following protocol may be employed. The yeast culture (an aqueous suspension of cells) is mixed with oil to form a water in oil emulsion in which, e.g., $10^6$ cells are present per 1 mL of emulsion. This provides $10^4$ strains each present represented by an average of 100 cells. This emulsion contains emulsion droplets ('bubbles') such that the vast majority of bubbles contain either no cells or one yeast cell (FIGS. 11, 12, and 15). An average emulsion droplet that is 10 microns in size encapsulates a 4 nanoliter PCR reaction. The distribution of the number (x) of cells per emulsion droplet behaves according to a Poisson probability distribution of the form $$p(x, l) = \frac{l^x e^{-l}}{x!},$$

where l equals the number of cells in a volume equal to the typical volume of an emulsion droplet. It has been empirically determined that cells diluted such that l is less than or equal to 0.01 rarely yields more than one cell per emulsion droplet. An early primer extension step is then performed to produce strands that are complementary to template DNA containing each of the barcode tags. Suitable primers are used to introduce overlap sequences that complement one another and allow later stitching of barcode-containing amplicons. In this way, multiple barcodes present in a cell may be covalently attached within a single short PCR product (See FIG. 13). The stitched barcodes are then amplified using primers at the 5' and 3' ends of the stitched barcode crossover PCR product. At this stage, the PCR products are extracted from the emulsion, sequenced and analyzed. Combinations of alterations that provided the greatest selective advantage (or least disadvantage) will be identified based on their increased (or decreased) representation in the pool relative to other gene combinations and/or relative to their representation in a pre-selection control population. Combinations of alterations that impart a large selective disadvantage in combination ('synergistic genetic interactions') often indicate compensatory or overlapping gene function. Additionally, one alteration may impart poor growth alone but increased growth (or a less severe growth reduction) in the presence of a second gene. These cases ('alleviating genetic interactions') often correspond to genes that act in concert or in series.

Example 2

Next-Generation Mapping of Genetic Interactions Applied to the Study of RNA Pol II Transcription Elongation When two genes are perturbed simultaneously, a surprising phenotype often emerges. Genetic interaction—defined by this phenomenon—indicates that the interacting genes have related functions. Genetic interactions have shaped our understanding of nearly all known biological pathways. Examples of genetic interaction encompass complex human diseases such as cancer that require multiple mutations.

Due to its facile genetics, *S. cerevisiae* has been a key model organism for the systematic study of genetic interactions. Of particular value to studying genetic interactions is a collection of deletion strains corresponding to all non-essential yeast genes, in which the deleted gene has been replaced with a selectable marker flanked by two gene-specific 'barcode' sequences. A 'synthetic genetic array' (SGA) approach (Scherens and Goffeau (2004) *Genome Biol.* 5:229; Tong et al. (2004) *Science* 303:808) has been used to find genetic interactions by systematically crossing pairs of deletion strains. Genetic interactions are identified by comparing the growth of doubly-deleted progeny with growth of each single mutant alone. Surprisingly slow growth (or non-growth) of the double mutant indicates a synergistic interaction, while surprisingly rapid growth indicates an alleviating interaction (e.g., suppression).

Another variant approach, "diploid-based synthetic lethality analysis with microarrays," or dSLAM (Pan et al. (2004) *Mol Cell.* 16:487; Pan et al. (2006) *Cell* 124:1069), combines deletion mutations by introducing a single 'query allele' by transformation en masse into a pool of diploid strains each carrying a different heterozygous deletion. The transformed pool is subsequently sporulated to obtain a pool of haploid double-mutant strains. After the resulting strain pool is grown competitively, a microarray is used to measure the relative abundance of each DNA barcode (and thereby the abundance of each corresponding strain).

Large-scale efforts by multiple groups have been able to test less than 10% of all gene pairs for genetic interaction by SGA, E-MAP (a variant of SGA (Schuldiner et al. (2005) *Cell* 123:507; Collins et al. (2006) *Genome Biol.* 7:R63; Collins et al. (2007) *Nature* 446:806)) and dSLAM approaches. These studies have been useful in the fields of DNA repair, cytokinesis, cell wall biosynthesis, chromatin regulation and transcription, pointing the way to many subsequent discoveries (Tong et al. (2004) *Science* 303:808; Schuldiner et al. (2005) *Cell* 123:507; Collins et al. (2007) *Nature* 446:806; Tong et al. (2001) *Science* 294: 2364; Bader, G. D., Tong, A. H., Zhang, L. V., Roth, F. P., Andrews, B. & Boone, C., "Exploiting synthetic genetic interactions to predict pathways and complexes," in *Protein-Protein Interactions: A Molecular Cloning Manual* (ed. Golemis, E.) (CSHL Press, New York, 2005); Keogh et al. (2006) *Genes Dev.* 20:660; Krogan et al. (2003) *Mol. Cell Biol.* 23:4207).

Technology that can more efficiently map genetic interactions would accelerate completion of the current interaction mapping effort to encompass all approximately 18 million gene pairs. Moreover, genetic interactions are strongly influenced by environment. At least half of all genetic interactions amongst DNA repair genes are missed unless DNA-damaging agents are present (St Onge et al. (2007) *Nat. Genet.* 39:199). Thus, the global map of interactions should ultimately be determined under hundreds of environmental conditions.

Recent advances in next-generation DNA sequencing technology have reduced the cost of sequencing short sequence tags by at least a factor of 1000 relative to conventional Sanger dideoxy sequencing coupled with electrophoresis. Additional future improvements are imminently expected. According to embodiments of the present invention, next-generation sequencing technology is used to improve the efficiency of genetic interaction mapping, using a "barcode fusion genetics" (BFG) strategy outlined in FIG. 1. The BFG approach is used to study factors influencing RNA polymerase II transcription elongation.

Networks of genetic interactions derived from combinatorial genetic perturbation have been analyzed (Tong et al. (2004) *Science* 303:808; Bader, G. D., Tong, A. H., Zhang, L. V., Roth, F. P., Andrews, B. & Boone, C., "Exploiting synthetic genetic interactions to predict pathways and complexes," in *Protein-Protein Interactions: A Molecular Cloning Manual* (ed. Golemis, E.) (CSHL Press, New York, 2005); Wong et al. (2004) *Proc. Natl. Acad. Sci. USA* 101: 15682; Wong and Roth (2005) *Genetics* 171:829; Wong et al. (2005) *Trends Genet.* 21:424; Zhang et al. (2005) *J. Biol.* 4:6). See also a large-scale study of synthetic sick or lethal interactions led by C. Boone (Tong et al. (2004) *Science* 303:808). Recurring patterns of connectivity have been described ('network motifs') relating genetic interaction with protein interaction, sequence homology, and other biological relationships (Zhang et al. (2005) *J. Biol.* 4:6); drawn conclusions about the role of transcription in mechanisms of robustness (Wong and Roth (2005) *Genetics* 171:829); and showing that protein and genetic interactions are highly complementary in their ability to identify functional relationships (Wong et al. (2005) *Trends Genet.* 21:424). Genetic interaction and the use of genetic interactions to order genes in pathways have been defined (St. Onge et al. (2007) *Nat. Genet.* 39:199; Mani et al. (2008) *Proc. Nat. Acad. Sci. USA* 105:3461).

Figure 2:
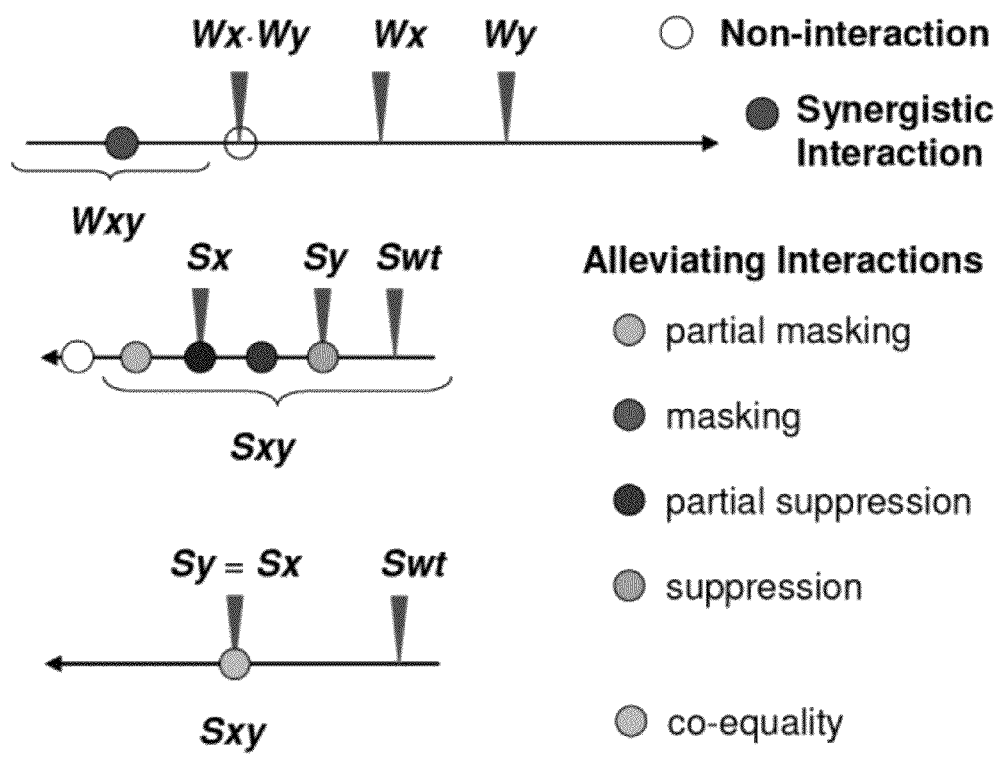
FIG. 2 schematically depicts a system for classifying genetic interactions. Interactions between genes x and y are established using quantitative fitness (W) and drug sensitivity (S) measurements of single and double mutants. This system is defined in St Onge et al. (2007) *Nat. Genet.* 39:199.
Figure 3:
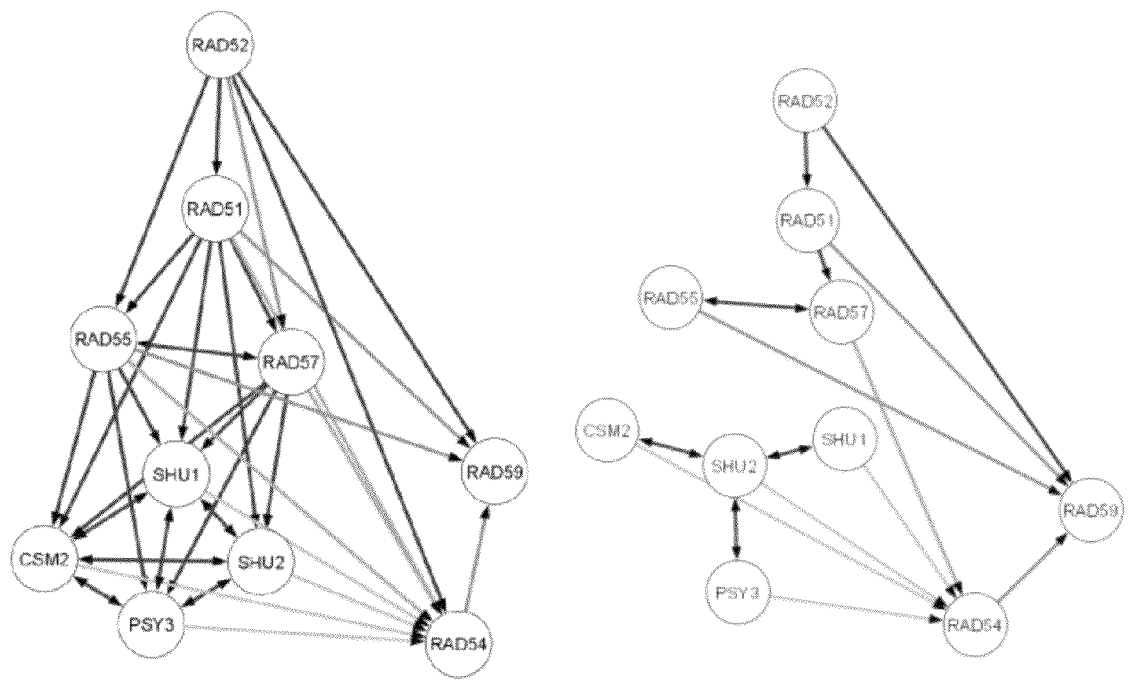
FIG. 3 depicts a network of alleviating genetic interactions derived for genes in the RAD52 epistasis group (left). Here, pruning algorithms were used to automatically eliminate interactions providing redundant information, thus simplifying the interpretation. The color scheme is the same as for FIG. 2. Arrows for asymmetric interactions are drawn from the predominant gene (i.e., the gene with the single mutant fitness most similar to the double mutant fitness) towards the other (masked or suppressed) gene.
Figure 4:
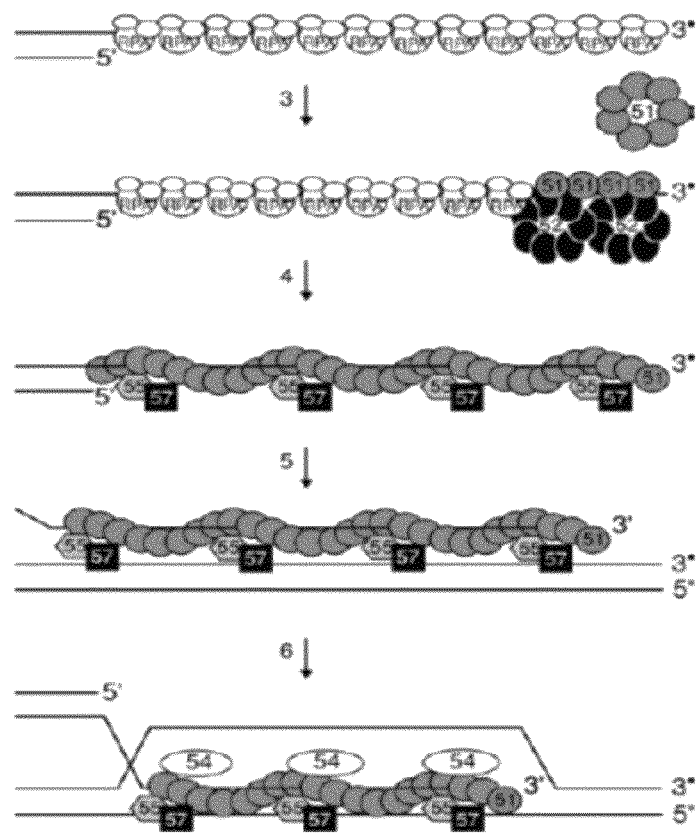
FIG. 4 schematically depicts many features of the current model for homologous recombination DNA repair that are captured by the automatically generated genetic interaction map derived from quantitative genetic interactions described herein. The order of action here can be compared with Rad52→Rad51→[Rad55, Rad57]→Rad54 in FIG. 3.

Quantitative interaction data can be used not only to identify parallel or compensatory relationships between genes via synergistic ('synthetic') interactions, but alleviating interactions can also provide clues about order of action in a biological pathway. FIG. 2 summarizes types of genetic interaction. FIG. 3 shows all alleviating interactions amongst a subset of DNA repair genes (left panel) and a version of the same graph in which interactions providing redundant information have been removed using the positive regulatory assumption (right panel) (Avery and Wasserman (1992) *Trends Genet.* 8:312; Zupan et al. (2003) *Bioinformatics* 19:383; Demsar et al. (2001) *Medinfo* 10:956). In the case of systematically-tested genes involved in homologous recombination repair, the simplified network of alleviating interactions closely approximates current knowledge based on more traditional studies (FIG. 4; from Broomfield et al. (2001) *Mutat. Res.* 486:167).

Genetic interactions have been used to reveal transcriptional mechanisms. Greenblatt, Krogan and colleagues have used a combination of SGA/E-MAP analysis (Schuldiner et al. (2005) *Cell* 123:507; Collins et al. (2006) *Genome Biol.* 7:R63; Collins et al. (2007) *Nature* 446:806; Schuldiner et al. (2006) *Methods* 40:344), tandem-affinity purification (TAP) of protein complexes (Krogan et al. (2006) *Nature* 440: 637; Collins et al. (2007) *Mol. Cell Proteomics* 6:439), and microarray expression analysis (Krogan and Greenblatt (2001) *Mol. Cell Biol.* 21:8203) to cluster factors thought to be important for gene expression and chromatin modification. In vivo and in vitro experiments have been carried out to verify interactions and make downstream mechanistic discoveries. For example:

1. Using E-MAP genetic interactions (Collins et al. (2007) *Nature* 446:806), genes were clustered according to similarity of their interaction partners. Histone H2A variant H2A.Z (Htz1) was clustered with a predicted chromatin remodeler known as Swr1. TAP purification showed Swr1 was part of a larger complex. Follow-up experiments showed that the SWR complex was essential for assembling Htz1 into chromatin (Krogan et al. (2003) *Mol. Cell Biol.* 23:4207). Based on a combination of E-MAP clustering and biochemical experiments, it was also shown that Htz1 is acetylated by the NuA4 complex (Keogh et al. (2006) *Genes Dev.* 20:660).

2. The E-MAP data indicated that Swr1 and Htz1 might have a role at double-stranded DNA breaks (DSBs), a prediction verified by in vivo experiments (Krogan et al. (2004) *Proc. Natl. Acad. Sci. USA* 101:13513). It is well known that DSBs trigger specific phosphorylation of histone H2A by the ATM/ATR kinases (Mec1/Tel1 in *S. cerevisiae*). Again, a combination of high-throughput genetic interaction and other data with directed experiments identified a key phosphatase that is essential for reversing this modification and restoring the cell cycle (Keogh et al. (2006) *Nature* 439:497; Chowdhury et al. (2005) *Mol. Cell* 20:801).

3. E-MAP clustering put the histone methyltransferase Set2 near chromodomain protein Eaf3 and PHD domain protein Rco1. PHD and chromodomains are thought to recognize methylated lysines. TAP purifications found Eaf3 and Rco1 to be in a previously-unknown complex with the histone deacetylase Rpd3/Sin 3. Experiments demonstrated methylation of histone H3 by Set2 was necessary to recruit the Rpd3C(S) complex to chromatin, thereby triggering a localized deacetylation (Keogh et al. (2005) *Cell* 123:593).

Preliminary steps towards barcode fusion genetics includes the BFG approach to genetic interaction mapping illustrated in FIG. 1 and outlined below. Step A is the generation of pools of haploid double-mutant deletion strains. The ability to produce pools of single-mutant deletion strains has been amply demonstrated (Giaever et al. (2002) *Nature* 418: 387). Production of complex pools of multi-mutant haploid strains by en masse mating and sporulation using SGA markers (Tong et al. (2004) *Science* 303:808) has been carried out.

In Step B, the resulting strain pool is grown competitively. The feasibility and value of competitive growth phenotyping of single-mutant and double-mutant strain pools has been abundantly demonstrated (Pan et al. (2004) *Mol Cell.* 16:487; Pan et al. (2006) *Cell* 124:1069; Giaever et al. (2002) *Nature* 418:387; Giaever et al. (2004) *Proc. Natl. Acad. Sci. USA* 101: 793).

Figure 6:
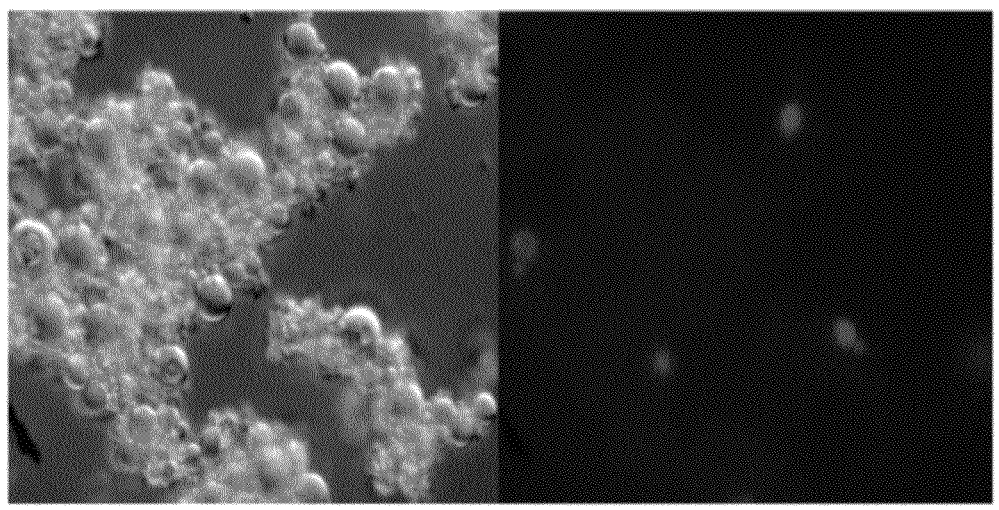
FIG. 6 depicts preliminary data showing single yeast cells encapsulated in aqueous droplets within a water-in-oil emulsion, with droplets indicated in the left panel and approximately corresponding locations of yeast cells indicated in the right panel (yeast cells are expressing the red fluorescent protein (RFP)).

In Step C, a dilute aqueous suspension of pooled yeast cells from Step B is combined with a specific mixture of oil and surfactants, such that an emulsion of water-in-oil droplets containing encapsulated yeast cells is produced. The concentration of cells is chosen so that the presence of more than one yeast cell in a droplet is rare, so that fused barcodes produced in Step D represent two mutations within the same cell. FIG. 6 (left panel) shows an emulsion with encapsulated yeast cells produced using an adaptation of an existing emulsification protocol (Williams et al. (2006) *Nat. Methods* 3:545). The position of fluorescent RFP-expressing encapsulated cells is also indicated (FIG. 6, right panel).

In addition to containing yeast cells, emulsion droplets generated in Step C also contained biochemical reagents necessary to amplify and fuse DNA barcodes via PCR. In Step D, after lysing yeast cells by heating the emulsion, the released genomic DNA is subjected to PCR via thermal cycling of the emulsion. PCR within emulsions has been previously demonstrated. Id. Barcodes at two distinct genomic loci are amplified and fused via a complementary DNA sequence in the "inner" primers that amplify two fragments (see FIG. 1). Preferential amplification of the fused product results from "outer" primer concentrations that are substantially higher than the "inner" primers required for the shorter 'pre-fusion' amplicons.

Regarding step D, fusion PCR has been used to connect yeast deletion collection barcodes within emulsions with no cells, using a mixture of barcode DNA as template. Barcode fusion PCR has been accomplished using yeast cells as the source of template DNA (without emulsion) at a volume-volume ratio approximating that in an emulsion droplet with a single cell. Barcode fusion PCR has been accomplished within an emulsion of encapsulated yeast cells, with the cells being the sole source of template DNA.

In Step E, the abundance of each strain in the double-mutant pool is estimated by sequencing fused barcodes. The use of barcode abundance as a proxy for strain abundance in competitively grown pools has previously been demonstrated in many publications (e.g., refs. Pan et al. (2004) *Mol. Cell.* 16:487; Pan et al. (2006) *Cell* 124:1069; Giaever et al. (2002) *Nature* 418:387; Giaever et al. (2004) *Proc. Natl. Acad. Sci. USA* 101: 793). The feasibility of extending this approach to fused barcodes through the adaptation of next-generation sequencing (instead of microarrays) to measure barcode abundance is discussed further in Research Design and Methods.

Research Design and Methods

1: "Barcode fusion genetics" (BFG) technology for efficiently mapping genetic interactions using next-generation sequencing.

The BFG technology has been outlined above and in FIG. 1. The following is carried out 1a) demonstration that fused barcodes are derived primarily from component barcodes that originated within the same cell; and 1b) it will be demonstrated that relative abundance of fused barcodes can be accurately and economically determined using a next-generation sequencing technology. Interactions amongst DNA repair genes for which we have already quantitatively measured the growth rate of all single- and double-mutants are searched (St Onge et al. (2007) *Nat. Genet.* 39:199).

Towards 1a, a 1:1 pool of two double-mutant strains is generated, collectively carrying four unique barcoded deletions (a yfg1Δ yfg2Δ strain and a yfg3Δ yfg4Δ strain). This represents a small-scale mockup of Steps A and B of the BFG process. Suspension in emulsion and PCR amplification (e.g., emulsion PCR) will be carried out as in FIG. 1 (Steps C and D). After verifying that PCR products have the proper length, fused barcodes will be shotgun-cloned, and 100 fused barcode clones will be isolated and sequenced by conventional Sanger sequencing. A control PCR will be carried out with cells in the absence of emulsion, such that barcodes from the same strain would be expected to fuse only 50% of the time in this experiment. We will judge the approach successful if the vast majority (greater than 90%) of fused barcode pairs are both derived from the same strain. If this test should fail, a possible explanation would be the presence of clumped or flocculent cells, or large emulsion droplets with multiple cells (although we have not yet seen evidence of these phenomena). Optimization of emulsion protocols and/or disaggregate cells by sonication could be done in response to failed tests (see, e.g., FIG. 16).

Towards 1b, 26 DNA repair genes are studied that have been previously quantitatively measured for exponential growth rates for all single- and double-mutant combinations (St Onge et al. (2007) *Nat. Genet.* 39:199). Barcoded KanMX-tagged deletion strains are available for all 26 genes, and barcoded NatMX-tagged strains are available for 9 genes.

One pool of 26 KanMX-tagged strains is generated and another of the 9 NatMX-tagged strains is generated. These haploid pools will be mated, and $Kan^R$ $Nat^R$ doubly-hemizygous diploid strains will be selected. These diploids will be sporulated and a pool of haploid doubly-deleted cells (potentially representing 189 distinct double-mutant strains) will be selected.

An aliquot of these cells (in log phase growth) will be kept as the '$t_0$' control, and two aliquots will be grown competitively—one for 5 wildtype generations ('$t_5$') and another for 15 wildtype generations ('$t_{15}$') and chilled to 4° C. Cells from $t_0$, $t_5$, and $t_{15}$ pools will suspended with PCR reagents and a water-in-oil emulsion will be formed. A 1% occupancy rate of cells in droplets should ensure that any given compartment contains at most one cell. Subsequent to thermal cycling, the aliquoted emulsion PCR mixture will be centrifuged to remove supernatant mineral oil and extracted with ethyl ether and ethyl acetate, and lyophilized. DNA will then be isolated, and PCR fragments of the appropriate length gel purified. PCR primers designed with AcuI sites, a Type IIS restriction enzyme cutting 14 bp away, leaving overhangs (2 bases from the barcode) for subsequent ligation to sequencing primers compatible with the Illumina 1G Genome Analyzer ('Solexa') instrument. The Solexa instrument is capable of sequencing 5 million paired-end reads (25 base pairs at each end) in one channel of one flow cell for approximately $1500. There are 8 channels per flow cell, so that 40 million paired-end reads might be obtained in a single 3-day run. Three channels of a run will be devoted to the $t_0$, $t_5$, and $t_{15}$ experiments for 1b.

The BFG approach can result in two copies of a single barcode amplicon fusing to form a 'self-self' barcode. Indeed, even if each fused barcode is derived from a single cell, 50% of all fused barcodes could be expected to be self-self. In certain exemplary embodiments, this 2-fold loss in efficiency can be reduced (e.g., use of KanMX- or NatMX-specific primers followed by circularization to bring fused barcodes close together). In other exemplary embodiments, the fraction of products that are self-self may be lowered by reduced amplification efficiency of self-self products due to increased efficiency of intramolecular hairpin formation by self-self products. The observation that products are not observed in some diagnostic PCR reactions in FIG. 18 suggests a reduced efficiency for self-self products. Each Solexa channel sequenced should provide 2.5 million informative paired reads, a greater than 10,000×'fold coverage' of each double-mutant strain for the 189 double-mutant experiment described above. Change in relative abundance within each pool will be compared with the change expected given the known exponential growth rates of each strain. In addition, the experiments can be repeated in silico by randomly sampling a subset of paired sequence reads to assess statistical power to detect genetic interactions as a function of fold-coverage.

Figure 8:
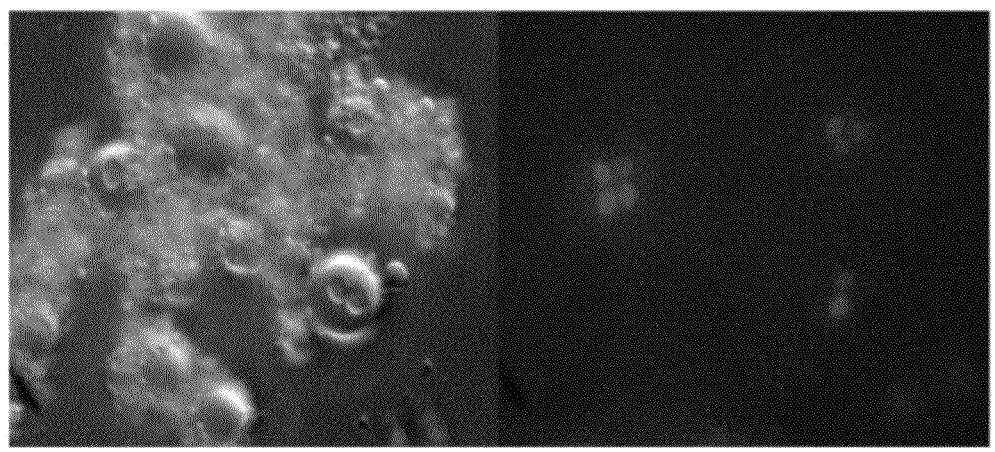
FIG. 8 depicts cells within water-in-oil emulsion droplets as in FIG. 6, with cell growth of one to two doublings allowed after encapsulation.

If the complexity of the fused barcode library is too low, emulsion PCR conditions can be optimized (e.g., temperature, primers, primer concentrations, addition of zymolyase to enhance cell lysis, etc). As shown (FIG. 8), cells can be grown within emulsion droplets post-encapsulation, effectively increasing the template concentration. The scale of the emulsion PCR reaction can be increased. In the extreme case, PCR can be effectively carried out in 50 ml reaction tubes.

One potential factor in this (and most other) genetic interaction methods is the presence of arising compensatory mutations (e.g., aneuploidy) that mask the deleterious effect of the original mutation. However, the strategy of Boeke et al. of freshly deriving parental haploids from diploid strains that are heterozygous in the deletion (thus reducing the deletion's fitness effects until the last moment) can be used.

Another issue is that genes with slow-growing single-mutants will generally have slow-growing double-mutants that will generally be overtaken by faster-growing strains. This complicates detection of synergistic interactions involving these genes (it will be hard to detect double-mutants growing more slowly than expected). To avoid this issue, several different single-mutant strain pools can be constructed, each with approximately equal growth rate. Double-mutant pools will be constructed by crossing these single-mutant pools, and subjected separately to competitive growth. These double-mutant pools would be expected to have approximately uniform growth rate except where there is genetic interaction. These same-growth-rate double-mutant pools can then be pooled such that the number of cells contributed from each same-growth-rate pool is proportional to the number of unique double-mutants it contains.

In one embodiment, BFG interaction mapping can be used to identify known and novel factors involved in RNA polymerase II transcription elongation. Several factors make this an ideal choice. First, multiple pathways and dozens of factors are involved. Not only do several factors directly impinge upon the RNA polymerase II catalytic rate, but also many other factors affect elongation by interacting with the nascent transcript or perturbing the chromatin template. How these various proteins interact with one another remains unclear and a comprehensive set of genetic interactions would be very informative. A second reason is that an SGA/E-MAP approach to map genetic interactions between a subset of the relevant gene has been previously used permitting comparison and validation of the BFG approach. However, because of the efficiency of the BFG approach, multiple growth conditions rather than the single one used in the E-MAP study can be analyzed.

Factors involved in transcription elongation and its interaction with chromatin can be determined with the BFG approach. In particular, a recently-discovered family of histone demethylases, the JmjC proteins can be studied. There are five JmjC proteins in yeast, each of which has homologues in other eukaryotes. Two of the proteins (Rph1 and Jhd1) are involved in transcription elongation (Kim and Buratowski (2007) *J. Biol. Chem.* 282:20827). A third protein, Jhd2, appears to function at promoters although its function remains unclear (Huarte et al. (2007) *J. Biol. Chem.* 282: 21662). None of the yeast JmjC proteins are essential and deletion strains typically have no strong phenotypes. Therefore, these are ideal candidates for the BFG approach. A matrix of double mutants for interactions is tested. In addition to the single growth condition used for E-MAP experiments, growth at more extreme temperatures (15° C. and 37° C.) is tested. An analysis in the presence of 6-azauracil and/or mycophenolic acid is performed. These chemicals cause an imbalance in the intracellular NTP pools. Strains with mutations that affect elongation are typically sensitized to these toxins, presumably due to reduced elongation rates caused by insufficient NTPs.

Simulations indicate that 100-fold coverage of fused barcodes will achieve sensitivity that approximates other genetic interaction screening methods. With 5 million non-self fused barcodes, each channel of a Solexa instrument should permit the assessment (for a given time point and growth condition) of 25,000 double-mutant strains. For example, a pool of all double-mutants among 96 genes (4560 unique double-mutants) might be assessed at greater than 1000-fold coverage in a single channel. This could be performed in each of several environmental conditions, e.g., those described above. The corresponding barcoded haploid deletion strains can been obtained from Jef Boeke's heterozygous diploid URA3-tagged deletion collection (Open Biosystems), pooled, and crossed to the corresponding (complementary mating type) pool of KanMX-tagged deletions from the standard library.

The BFG approach could be applied to other double perturbations and other organisms. For example, a set of 2μ high-copy number plasmids is used, each carrying a specific yeast gene under its endogenous promoter flanked by barcode sequences. Thus, the BFG approach could be applied to globally map high-copy suppressors of deletion alleles. The BFG approach could also produce a global map of complex haploinsufficiency interaction (CHI), an interaction between two heterozygous null loci within a diploid cell. CHI interactions have been shown to often correspond to protein interactions (Baetz et al. (2004) *Mol Cell Biol.* 24:1232; Haarer et al. (2007) *Genes Dev.* 21:148) (reviewed by Komili & Roth (2007) *Genes Dev,* 21:137). In another example, pooled siRNA or shRNA reagents could be applied to human cells which would then be selected e.g. by FACS for particular phenotypes. Fused barcodes could then identify specific combinations of RNAi reagents that led to the phenotype. The BFG approach could also be used to screen barcoded strain pairs for successful complementation in mate assays such as yeast two-hybrid, where for example each barcode corresponds to a component of the AD/DB reporter system carrying a specific engineered gene fused to either the activation domain (AD) or DNA-binding domain (DB) of a transcription factor capable of activating a reporter gene (See Walhout et al. High-throughput yeast two-hybrid assays for large-scale protein interaction mapping. *Methods* (2001) vol. 24 (3) pp. 297-306).

With current Solexa sequencing technology, the BFG method could potentially map a global genetic network at ~$600K per growth condition (12.5×10$^6$ gene pair×100 reads/double-mutant×2 time points×Solexa run/40M reads× $10,000/Solexa run) in less than a year. Furthermore, the per-read cost is likely to drop rapidly given anticipated advances in next-generation sequencing technology.

Example 3

The BFG Procedure Specifically Fuses Barcodes Originating within the Same Cell and does not Fuse Barcodes Originating from Different Cells An important feasibility test has been performed showing that the BFG procedure specifically fuses barcodes originating within the same cell, but does not fuse barcodes originating from different cells. This test also provides evidence that uninformative 'self-self' barcode fusions are disfavored.

Emulsified Barcode Fusion PCR from a Strain Mixture

Figure 16:
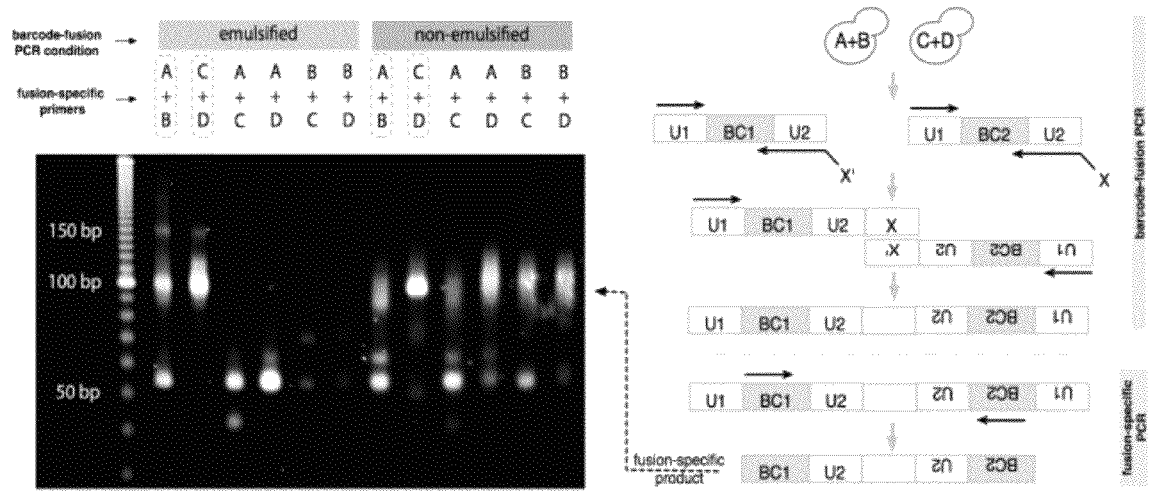
FIG. 16 depicts that stitched barcode products and successful PCR amplification could be obtained within an emulsion using cells as a source of template DNA, and that barcode fusions corresponding to double-deletion yeast strains could be uniquely identified with barcode-fusion emulsion PCR directly from cells. Pairs of barcodes A+B (from strain RY0391) and C+D (from strain RY0392) are contained in the two double-deletion strains used. Emulsified and non-emulsified barcode-fusion PCR was performed on a mixture of the cells from the two strains by the scheme shown at right. Afterward, a 400×-diluted product of barcode-fusion PCR was amplified using diagnostic primers complementary to specific barcode sequences to assess the presence of specific barcode fusion products. At left, a gel indicates presence or absence of each of six specific barcode fusion products in both the emulsified and non-emulsified reactions. The assay of the emulsified reaction shows that only the specific barcode fusion products representing the original yeast strains are present, whereas in the non-emulsified reaction assay, all six possible barcode fusion products are detected. The results indicate that the barcode fusion PCR reaction in emulsion specifically 'stitches' barcode pairs that originate from the same cell.

To evaluate whether barcodes could be successfully fused and amplified in emulsion directly from double-deletion yeast strains to yield only fusion projects that corresponds to double-mutant genotypes within a studied cell population, two MATα double-deletion strains (RY0391 and RY0392) were mixed. These strains each carry deletions for a unique pair of genes (arbitrarily chosen), and were created in the Roth Lab from mating and sporulation of corresponding single deletion strains obtained from the Yeast Deletion Collection. RY0391 carries barcodes A (pdr12Δ) and B (yol075cΔ), and RY0392 carries C (adp1Δ) and D (nft1Δ). Cells were mixed at equal concentrations (5,000 cells/μL for each strain) and subjected to barcode-fusion PCR (using methods described herein), either within an emulsion using encapsulated cells as template, or in the absence of emulsion within an unconstrained suspension of cells. The fused product from each experiment was queried in turn with specific combinations of barcode-specific primers that identify each of six possible fusion products. Ideally, as there should be at most one yeast cell per emulsion droplet, the barcode fusion products generated in emulsion should correspond only to barcodes that existed together in any particular yeast cell (i.e., A+B and C+D). Presence of other barcode fusions (i.e., A+C, A+D, B+C and B+D) would indicate either 1) that the yeast cells are not well compartmentalized, allowing undesirable fusion products that do not represent the source strains, or 2) that self-self fusion products (e.g., barcode A fused to barcode A) were present. The desired result was obtained (FIG. 16). Specifically, using the BFG approach, fused products corresponding only to barcodes arose from a single cell type, whereas all assessed fusion products were produced under the control non-emulsified conditions. This experiment demonstrates that multiple yeast strains carrying specific pairs of deletions can be unambiguously identified using the BFG procedure.

Absence of Self-Self Fusion Products

As discussed above, there is the potential for a two-fold reduction of cost-efficiency of the BFG process due to the generation of uninformative self-self products. Without being limited by scientific theory, it was hypothesized that self-self products may be highly disfavored given that they would be expected to form tight hairpins with a resultant decrease in the efficiency of their amplification. Indeed, although each of the diagnostic PCR reactions shown in FIG. 16 had the opportunity to amplify self-self products (e.g., the A+B diagnostic reaction might have also amplified A-A fusions and B-B fusions), no products were observed in the emulsified PCR experiment in the A+C, A+D, B+C or B+D lanes, indicating that uninformative self-self fusion products will not represent major issue.

Illumina/Solexa Genome Analyzer

An Illumina/Solexa Genome Analyzer has been used to produce approximately 950 Mbp of raw sequence data at an accuracy of 99.5% from a single run.

Additional Experiments

Having shown that the BFG process can produce specific fusion products that uniquely identify yeast strains, the extent to which quantitative measurement of fused-barcode abundance reflects the concentration of yeast cells used as templates for the BFG process has been investigated. A library of barcode-fusion PCR products is currently being prepared that will be used to assess the quantitative yield of barcode-fusion products from a similar two-strain mixture as discussed above. Using defined concentration ratios of the two template strains over a wide range of concentration ratios, emulsified fused-barcode products are being generated that will be cloned, transformed into bacterial cells and sequenced via Illumina/Solexa or traditional Sanger sequencing. Without being limited by scientific theory, it is anticipated that approximately 300-400 clones for Sanger-based sequencing will be sequenced for this purpose to help determine empirically the eventual sequencing depth that will be needed to assay more complex populations of strains. Assuming that this validation experiment is successful, subsequent scale-up experiments using more complex strain mixtures will be performed on the Illumina/Solexa instrument.

Example 4

Protocol for Clonal Amplification and Sequencing of Stitched DNA Barcodes from Heterogeneous Double-Deletion *Saccharomyces cerevisiae* Strains Haploid single-gene deletion yeast strains carrying uniquely identifying 20-base DNA barcodes are available from the Yeast Deletion Project collection, representing over 5,000 genes not required for growth on rich media.

One-Step Overlap Extension PCR of Barcodes

Each gene deletion locus in the Yeast Deletion Collection has been previously replaced with a selectable marker cassette containing the G418 resistance marker KanMX4 as well as a 5' 20-bp DNA barcode (UPTAG). The UPTAG is flanked by a pair of universal primer binding sites both upstream (U1; 5'-GATGTCCACGAGGTCTCT (SEQ ID NO: 1)) and downstream (U2; 5'-CGTACGCTGCAGGTCGAC (SEQ ID NO:2)). "Switcher" plasmids are available that enable changing the resistance marker cassette at the deletion locus to confer resistance to nourseothricin (NatMX4) or 5-fluoro-orotic acid (Ura3MX4). The well-established SGA approach developed by Boone and colleagues enables the mating of strains with alternative resistance alleles at different deletion loci in combination with subsequent sporulation and haploid selection. The SGA protocol permits efficient creation of doubly-deleted haploid strains that lack two distinct genes—and, importantly, are tagged by two distinct DNA barcodes at each deletion locus.

The barcodes in a double-deletion strain can be amplified as a fused single sequence using one-step overlap-extension PCR (OOE-PCR), a process which permits a single PCR reaction to be used to first amplify fragments containing each barcode separately, and then amplify a fusion product containing both fragments. Each barcode fragment is amplified by primers binding to U1 and U2, respectively. One primer sequence P1 (5'-AGAGACCTCGTGGACATC (SEQ ID NO:3)) binds to U1. Two different primers bind to U2, these being P2-X (5'-GTCGACCTGCAGCGTACG-X-3' (SEQ ID NO:4)) and P2-X' (5'-GTCGACCTGCAGCGTACG-X'-3' (SEQ ID NO:5)). P2-X and P2-X' are engineered with unique and complementary 20-bp 5' sequence tags (X and X', X=5'-GCTGTCGTCGCTACTATTA-3' (SEQ ID NO:6), X'=5'-TAATAGTAGCGACGACAGC-3' (SEQ ID NO:7)) which leads to generation of individual barcode amplicon fragments having 3' complementarity. Alternately, the sequence composition of X and X' can be varied to produce different amplicon fragments that have longer or shorter 3' complementarity or sequence-specificity, or complementarity that exhibits higher or lower annealing temperature upon hybridization. The length and sequence of the complementary region can be varied to enhance or decrease the competition of primer-template binding with primer-primer binding at given thermal conditions and primer concentrations.

During thermal cycling, primer P1 is used at concentrations of extreme excess (0.5-1.0 μM) compared to primers P2-X and P2-X' (5-10 nM). Because the P2 primers are limiting and diminish in concentration in successive rounds of thermal cycling, the difference in concentration biases later rounds of PCR towards preferential amplification of the longer fused product generated by overlap of the X and X' sequences. Amplification of the longer product is driven solely by primer P1. The bias toward longer product can be enhanced by using a "touch-up" thermal gradient during PCR thermal cycling. As further rounds of PCR proceed, the annealing temperature is raised to promote annealing between longer sequences.

Several variations can be used to optimally control the composition and length of stitched products generated by this approach:

A) Primer P1 is optionally engineered with a 5' tag containing an AcuI cut site immediately upstream of the U1 binding sequence. AcuI permits downstream off-site cutting to remove the U1 sequence of the final amplified product. This can also be used to generate an overhanging-ended product for efficient incorporation in an expression vector (e.g. BlueScript).

B) A shortcoming of the OOE-PCR approach outlined above is that it offers no preferential amplification of fused barcodes from different loci. At best, only half of the resulting stitched barcodes include barcodes from two different loci, and are useful in identifying the double-deletion strain of origin. This problem can potentially be overcome by exploiting the fact that the P1 primer site is directly upstream of the barcode, and using the 5' end of the barcode itself as part of the priming site. If double-deletion strains are picked and pooled such that they differ at the 5'-most end of their barcodes, two variants of each P1 primer can be used in each PCR reaction that differ by one or more corresponding bases at their 3' end. Assuming spurious mispriming events are rare, the OOE-PCR method would only generate full-length fused products that are from barcodes at different loci.

Preparation of Emulsion

Cells are grown to suitable density and pooled preparation for emulsion, and kept at 4° C. Typical haploid yeast culture densities represented by measurements of 0.1-1.0 ($OD_{600}$ in YPD) correspond (on average) to $10^6$ to $10^7$ cells per mL. Concentration estimates of viable aqueous compartments in emulsions of the type described here range from $10^8$-$10^9$ per mL. A 1% average occupancy rate of compartments by DNA fragments is sufficient to ensure with high probability that any given compartment contains at most one fragment. (Using the lower limit of $10^8$ as the estimated number of aqueous compartments, if $10^6$ cells are emulsified independently then the probability (Poisson, lambda=0.01, x>=2) that any single compartment contains more than one yeast cell is $5 \times 10^{-5}$.) To ensure that cells assort independently in emulsion and don't aggregate, the aqueous mixture is subjected to vortexing and/or brief sonication. Higher than normal concentrations of PCR buffer (NEB Taq Buffer, 1.5×) and dNTPs (0.5 mM each) are used to boost PCR yield.

The suspension of yeast cells and PCR reagents are then emulsified using an adaptation of the process described by Williams et al. (*Nature Methods* July 2006). Surfactants Triton X-100 (Sigma) (0.05% by volume) and ABIL EM 90 (Degussa) (2% by volume) are dissolved in molecular biology grade mineral oil (Sigma) and this mixture is kept ice-cold (4° C.). The ice-cold aqueous mixture of cells and PCR reagents is added dropwise to the oil mixture in a volume ratio of 1:9 over two minutes with magnetic stirring in a 1 mL cryovial (Corning) at 1400 r.p.m. with a 3×8 cylindrical stir bar with pivot point (VWR). The mixture is stirred for additional 5 minutes and then aliquoted in 0.2 mL quantities into five 0.5 mL thin-walled PCR tubes for thermal cycling.

Isolation and Characterization of Stitched Barcode Products

Subsequent to thermal cycling, the aliquoted emulsion PCR mixture is re-pooled within a 2 mL eppendorf tube, centrifuged (13,000 g, 5 min.) and supernatant mineral oil is removed. The product is then subjected to two-fold extraction with water-saturated ethyl ether (2×1 mL), single extraction with water-saturated ethyl acetate (1×1 mL) and further two-fold extraction with water-saturated ethyl ether (2×1 mL). The remaining organic solvent is removed by vacuum centrifugation (Speedvac) and the product is purified via Qiagen PCR Cleanup mini-prep, and analyzed via 3% low-melting point agarose gel electrophoresis.

Because the primers flanking the two barcodes in each strain are identical, the BFG approach can result in the amplified product of one barcode fusing to itself inside an emulsion droplet. This is expected to have little or no impact on accuracy of the eventual double-mutant fitness measurements (assuming adequate generation of fused product) it however reduces the efficiency and raises the cost of sequencing by a factor of two on a per strain basis. To reduce one barcode fusing to itself within the droplet, an additional two-nucleotide 'key' sequence is incorporated into the overlapping primers that corresponds to the adjacent first two nucleotides of the barcode sequence itself, helping to ensure that amplified product is specific to each barcode. The minor technical impediment to this approach is that strains would need to be pooled not only according to expected growth rates (as mentioned above) but also by the corresponding 'key' sequence at the barcodes.

What is claimed:

1. A method of determining the presence of at least one genetic mutation in a population of organisms, comprising the steps of:
   (a) creating one or more aqueous emulsion droplets, wherein at least one emulsion droplet includes an organism having at least one barcode-associated mutation;
   (b) performing a polymerase chain reaction (PCR) in the emulsion droplet to amplify at least one fused DNA product of one or more barcodes;
   (c) recovering the aqueous phase from the emulsion droplet, wherein the aqueous phase includes the amplified, barcode-associated mutation; and
   (d) detecting the presence of the amplified, barcode-associated mutation.

2. The method of claim 1, wherein the population of organisms is *S. cerevisiae*.

3. The method of claim 1, wherein the barcode-associated mutation includes a detectable label.

4. The method of claim 1, wherein the population of organisms includes a detectable label.

5. The method of claim 1, wherein the step of detecting is performed by sequencing the amplified, barcode-associated mutation.

6. The method of claim 1, wherein the step of detecting is performed by identifying the presence of a detectable label.

7. The method of claim 1, wherein the amplified, barcode-associated mutation is a genetic deletion or a genetic insertion.

8. The method of claim 1, wherein the barcode-associated mutation is present on a plasmid.

9. The method of claim 1, wherein the population of organisms includes at least 10 different barcode-associated mutations, and wherein for at least 95% of the organisms, each organism contains at least one barcode-associated mutation.

10. The method of claim 9, wherein for at least 95% of the organisms, each organism contains at least two barcode-associated mutations.

11. The method of claim 9, wherein for at least 95% of the organisms, each organism contains at least three barcode-associated mutations.

12. The method of claim 1, wherein the population of organisms includes at least 100 different barcode-associated mutations and wherein for at least 95% of the organisms, each organism contains at least one barcode-associated mutation.

13. The method of claim 1, wherein the population of organisms includes at least 1000 different barcode-associated mutations, and wherein for at least 95% of the organisms, each organism contains at least one barcode-associated mutation.

14. A method of identifying the genotype of a population of organisms in a mixture, wherein each single organism comprises a plurality of barcode-associated mutations therein, comprising the steps of:
   (a) subjecting the mixture to conditions where for each organism in the population, the plurality of barcode-associated mutations within the single organism are covalently linked together to create a stitched barcode representing the single organism;
   (b) amplifying the stitched barcode for each single organism; and
   (c) determining the identity of the stitched barcode for each single organism thereby genotyping each single organism in the population of organisms.

15. The method of claim 14, wherein the step of determining the identity is performed by detecting the presence of at least one detectable label in the stitched barcode.

16. The method of claim 14, wherein each barcode-associated mutation includes a detectable label.

17. The method of claim 14, wherein the organism is *S. cerevisiae*.

18. The method of claim 14, wherein the plurality of barcode-associated mutations includes at least one vector that expresses a gene encoding an RNA that is capable of inhibiting expression of an endogenous gene.

19. The method of claim 14, wherein the population of organisms are cells derived from *H. sapiens*.

20. The method of claim 18, wherein the population of organisms are cells derived from a mammal.

21. The method of claim 14 wherein the steps of subjecting the mixture to conditions and amplifying include creating a mixture of aqueous emulsion droplets, wherein the aqueous emulsion droplets each includes one organism having at least two barcode-associated mutations, covalently linking within the aqueous emulsion droplets a plurality of barcode-associated mutations from the organism together to create a stitched barcode representing the one organism and performing a polymerase chain reaction within the aqueous emulsion droplets to amplify the stitched barcode representing the one organism, and recovering the aqueous phase from the emulsion droplet, wherein the aqueous phase includes the amplified stitched barcode.

22. A method of identifying the genotype of a population of cells, wherein each cell comprises a plurality of barcode-associated mutations therein, comprising the steps of:
   forming an emulsion of droplets wherein a majority of droplets include at most one cell;
   lysing the cells within the droplets of the emulsion;
   linking the plurality of barcode-associated mutations together within the droplets of the emulsion to create stitched barcodes without contamination of DNA from other cells;

amplifying the stitched barcodes within the droplets of the emulsion without contamination of DNA from other cells; and determining the identity of the stitched barcode for each cell thereby genotyping each cell in the population of cells.

23. The method of claim 22, wherein the step of determining the identity is performed by detecting the presence of at least one detectable label in the stitched barcode.

24. The method of claim 22, wherein each barcode-associated mutation includes a detectable label.

25. The method of claim 22, wherein the cells are *S. cerevisiae* cells.

26. The method of claim 22, wherein the plurality of barcode-associated mutations includes at least one vector that expresses a gene encoding an RNA that is capable of inhibiting expression of an endogenous gene.

27. The method of claim 22, wherein the cells are mammalian cells.

28. The method of claim 22 wherein the cells are human cells.

* * * * *